(12) United States Patent
Lakin et al.

(10) Patent No.: US 7,780,739 B2
(45) Date of Patent: Aug. 24, 2010

(54) METHOD AND APPARATUS FOR USE OF A METAL-METAL CONSTRAINED LINER

(75) Inventors: Ryan C. Lakin, Warsaw, IN (US); Troy W. Hershberger, Winona Lake, IN (US); Michael S. Schular, Leesburg, IN (US); William J. Slone, Silver Lake, IN (US); Kim S. Parcher, Etna Green, IN (US); Phillip M. Gibbs, Winona Lake, IN (US); Aaron P. Smith, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1251 days.

(21) Appl. No.: 10/769,741

(22) Filed: Jan. 30, 2004

(65) Prior Publication Data

US 2004/0225369 A1 Nov. 11, 2004

Related U.S. Application Data

(63) Continuation-in-part of application No. PCT/US02/24271, filed on Jul. 31, 2002.

(60) Provisional application No. 60/308,881, filed on Jul. 31, 2001.

(51) Int. Cl.
*A61F 2/34* (2006.01)
(52) U.S. Cl. .................... 623/22.17; 623/22.24
(58) Field of Classification Search ............. 623/22.11, 623/22.15, 22.16, 22.17, 22.18, 22.19, 22.2, 623/22.21, 22.22, 22.24, 22.25, 22.28, 22.29, 623/23.13
See application file for complete search history.

(56) References Cited

U.S. PATENT DOCUMENTS

| 2,668,531 A | 2/1954 | Haboush |
| 3,067,740 A | 12/1962 | Haboush |

(Continued)

*Primary Examiner*—Ralph A Lewis
(74) *Attorney, Agent, or Firm*—Harness, Dickey

(57) ABSTRACT

An acetabular prosthesis and method for its use in an orthopedic surgery is disclosed. The acetabular prosthesis forms a metal bearing, which articulates with a femoral head. The acetabular prosthesis is also configured so as to accept a polymer constraining ring. Should a revision surgery be necessary, the acetabular prosthesis may accept a polymer bearing liner over the metal bearing. The polymer bearing liner then articulates with the femoral head.

34 Claims, 25 Drawing Sheets

U.S. PATENT DOCUMENTS

| | | |
|---|---|---|
| 3,584,318 A | 6/1971 | Scales et al. |
| 3,740,769 A | 6/1973 | Haboush |
| 3,815,157 A | 6/1974 | Skorecki et al. |
| 3,875,593 A | 4/1975 | Shersher |
| 4,619,658 A * | 10/1986 | Pappas et al. ............ 623/22.19 |
| 4,642,123 A | 2/1987 | Noiles |
| 4,676,798 A | 6/1987 | Noiles |
| 4,978,356 A * | 12/1990 | Noiles ..................... 623/23.4 |
| 5,019,105 A | 5/1991 | Wiley |
| 5,133,763 A * | 7/1992 | Mullers .................. 623/22.15 |
| 5,314,491 A | 5/1994 | Thongpreda et al. |
| 5,413,603 A * | 5/1995 | Noiles et al. ............. 623/23.43 |
| 5,425,779 A | 6/1995 | Schlosser et al. |
| 5,755,807 A | 5/1998 | Anstaett et al. |
| 5,800,555 A | 9/1998 | Gray, III |
| 5,824,108 A | 10/1998 | Huebner |
| 5,989,293 A | 11/1999 | Cook et al. |
| 6,042,611 A | 3/2000 | Noiles |
| 6,093,208 A | 7/2000 | Tian |
| 6,475,243 B1 * | 11/2002 | Sheldon et al. ........... 623/22.28 |
| 6,682,566 B2 * | 1/2004 | Draenert .................. 623/22.24 |
| 6,916,342 B2 * | 7/2005 | Frederick et al. ......... 623/22.29 |
| 2002/0068980 A1 | 6/2002 | Serbousek et al. |
| 2003/0125810 A1 * | 7/2003 | Sullivan et al. .......... 623/22.17 |

* cited by examiner

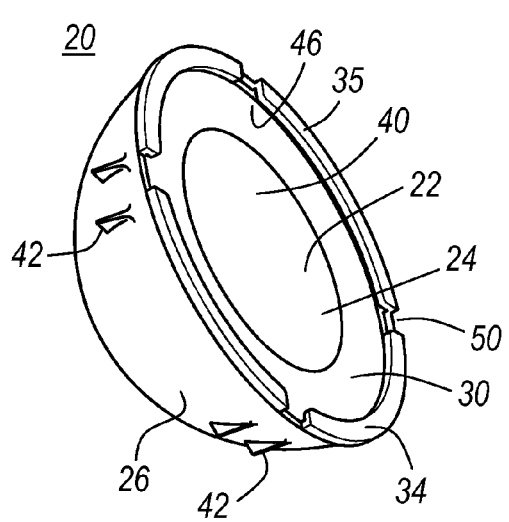
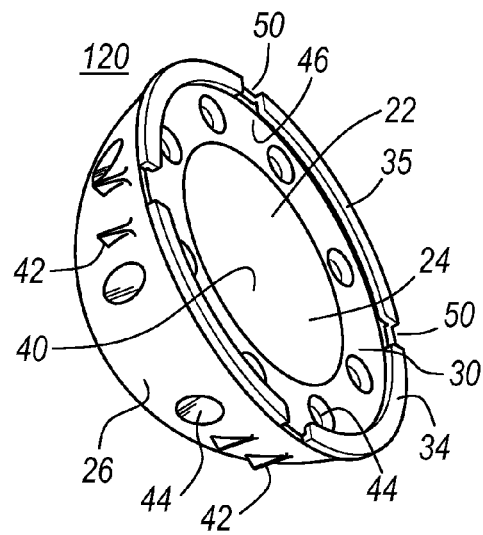
FIG. 1
FIG. 1A
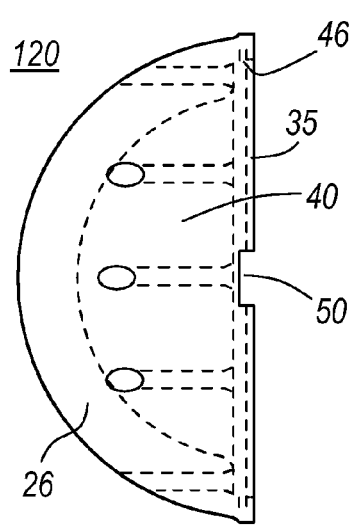
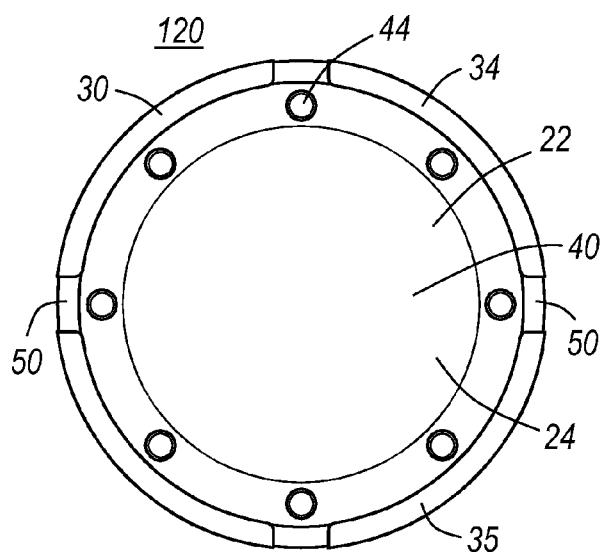
FIG. 1C
FIG. 1B

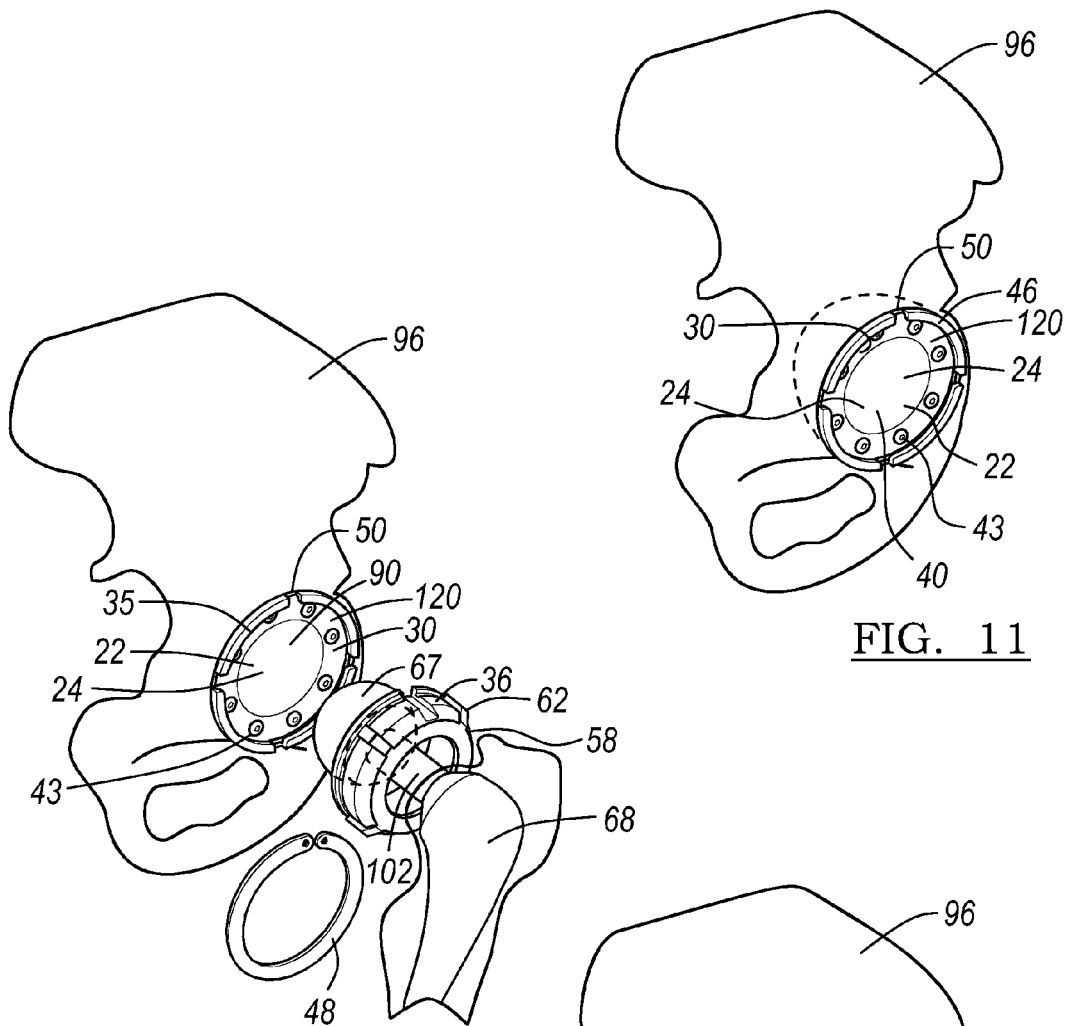
FIG. 10
FIG. 11
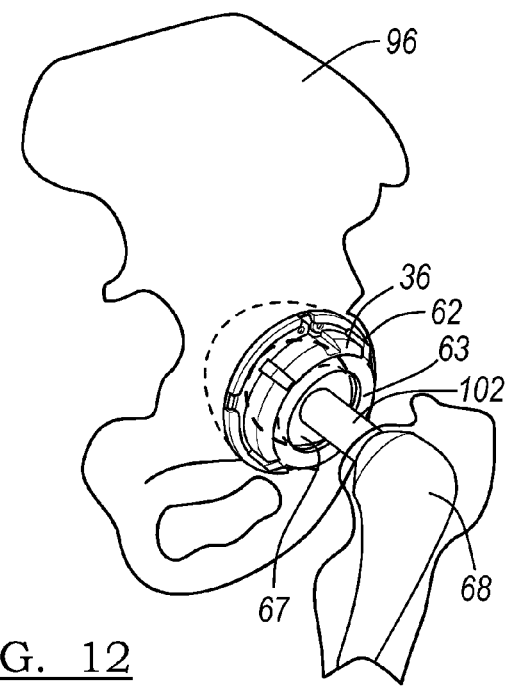
FIG. 12

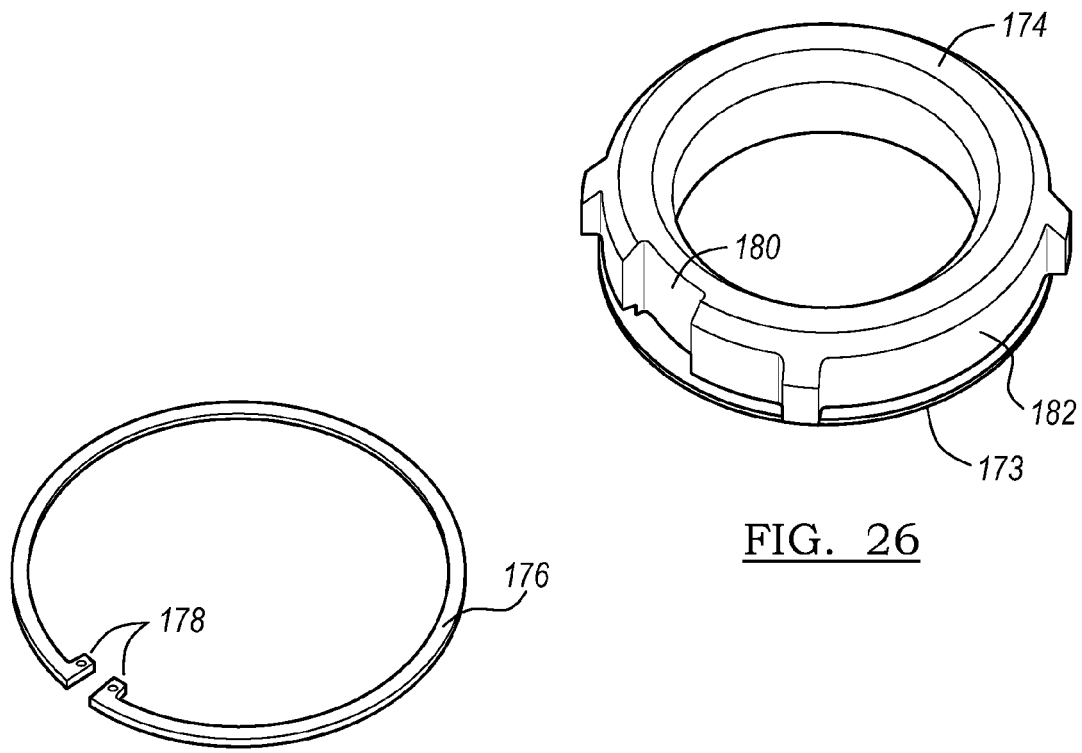
FIG. 26
FIG. 27
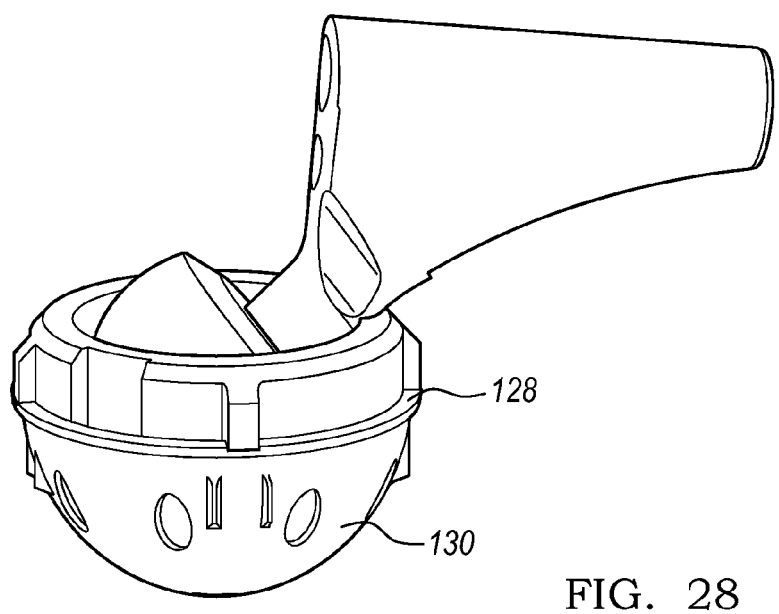
FIG. 28

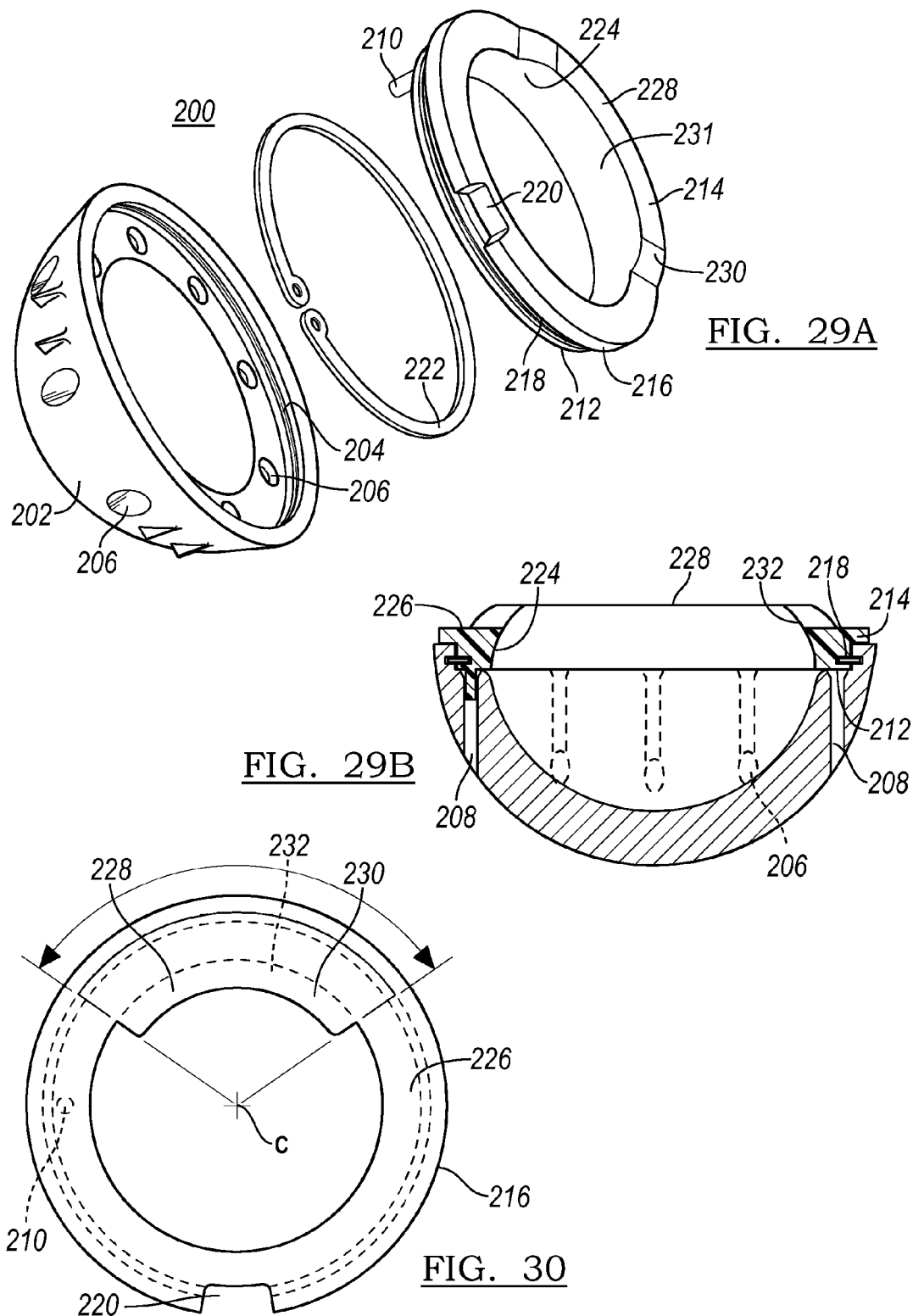

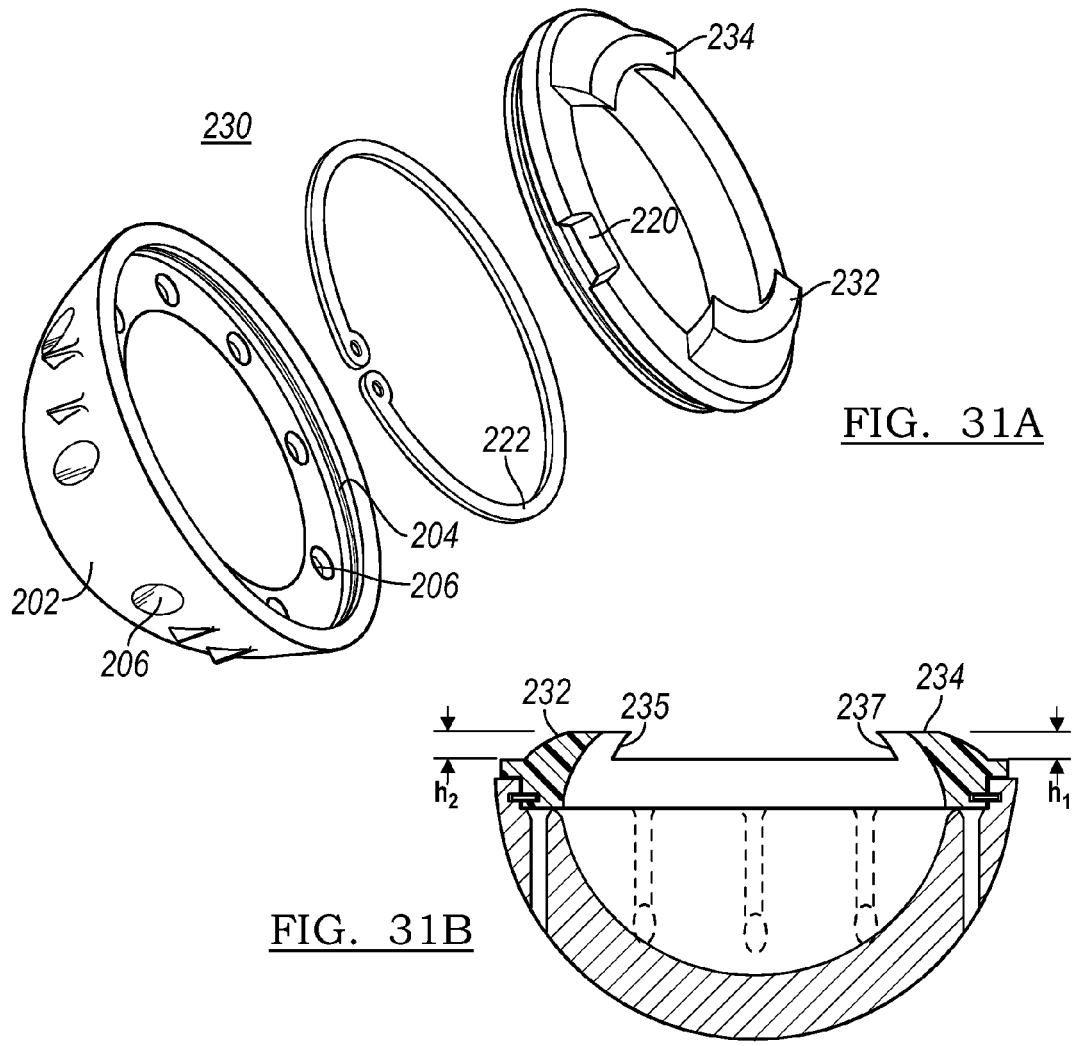
FIG. 31A
FIG. 31B
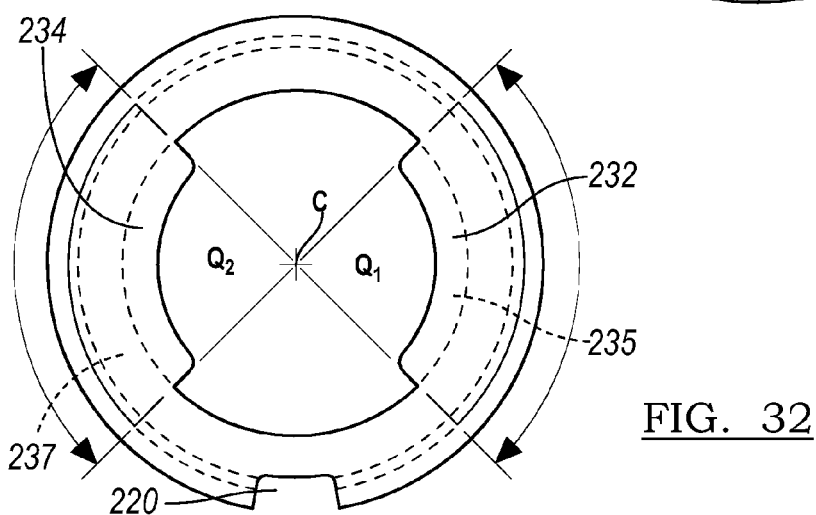
FIG. 32

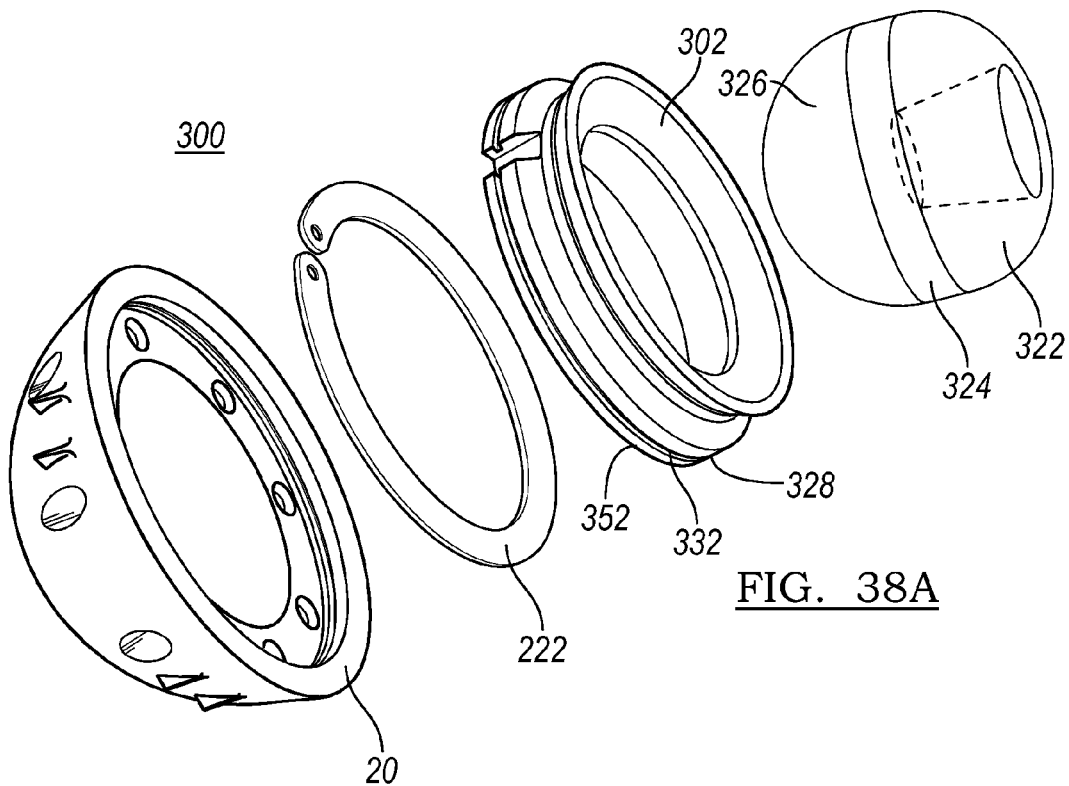
FIG. 38A
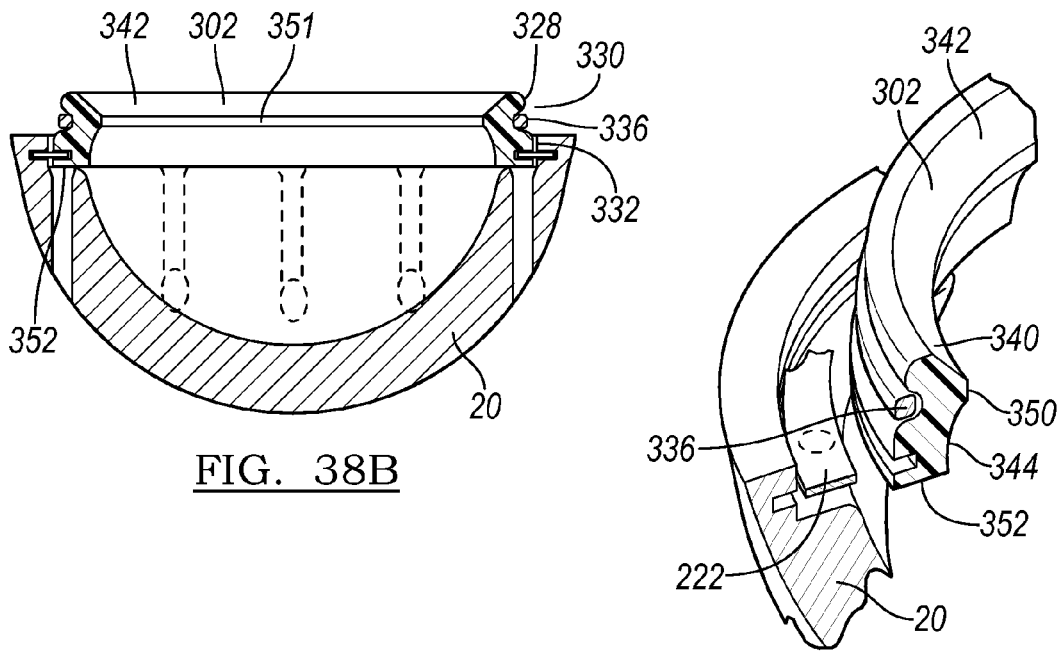
FIG. 38B
FIG. 38C

METHOD AND APPARATUS FOR USE OF A METAL-METAL CONSTRAINED LINER

CROSS-REFERENCE TO RELATED APPLICATIONS

This application is a continuation-in-part application of pending PCT International Application No. PCT/US02/24271 which was filed in the U.S. Receiving Office on Jul. 31, 2002. PCT International Application PCT/US02/24271 claims the benefit of U.S. Provisional Application No. 60/308,881, filed on Jul. 31, 2001. The disclosure of the above applications is incorporated herein by reference.

FIELD OF THE INVENTION

The present invention relates generally to a method and apparatus for use in orthopedic surgery and, more particularly, to a method and apparatus for providing an acetabular prosthesis that includes a metal-metal constrained liner having a metal bearing. The metal bearing is capable of receiving a polymer bearing insert for use during an initial or orthopedic surgical revision procedure.

BACKGROUND OF THE INVENTION

A natural hip joint may undergo degenerative changes due to a variety of etiologies. When these degenerative changes become so far advanced and irreversible, it may ultimately become necessary to replace a natural hip joint with a prosthetic hip. When implantation of such a hip joint prosthesis becomes necessary, the head of the natural femur is first resected and a cavity is created within the intramedullary canal of the host femur for accepting the hip prosthesis. The hip prosthesis may be inserted and supported within the host femur by cementing the hip prosthesis within the host femur. Alternatively, the hip prosthesis may be impacted into the host femur so that it is snugly fit and supported by the host femur. If the acetabulum also needs repair, all remnants of articular cartilage are generally removed from the acetabulum and an acetabular prosthesis, which will accommodate the head or ball of the hip prosthesis is affixed to the acetabulum. The acetabular prosthesis is affixed to the acetabulum by means of cement, screws or other appropriate fixation means.

Due to any number of reasons, however, a small portion of patients that undergo such orthopedic surgical procedures may require subsequent revision surgery to replace the prosthetic device with a new prosthetic device generally referred to as a revision prosthesis. Various types of revision acetabular prostheses are currently available and different surgeons prefer different types of revision acetabular prostheses. Some surgeons prefer to use what is known as an ilium flange that is formed integral with the acetabular prosthesis and enables further securement of the acetabular prosthesis in the ilium region of the pelvis. Other surgeons prefer to use what is known as an obturator hook that is able to provide inferior fixation of the acetabular prosthesis by engaging the obturator foramen which is a large aperture adjacent the acetabulum. Because of this, a hospital must maintain a large inventory of different revision acetabular cups to meet the various surgeons' preferences. Moreover, the surgeon will generally have to have several revision acetabular cups available during surgery to account for any type of condition that may arise during the surgical procedure. This increased inventory of prosthetic devices increases the overall hospital costs and inventory control. Furthermore, by requiring the multiple revision acetabular cups to be available during the surgical procedure, multiple prosthetic devices must be sterilized prior to the surgical procedure, thereby increasing the surgical time, cost and complexity.

What is needed then is a method and apparatus for providing a metal-metal constrained liner that may have the articulating bearing surface altered without requiring removal of the acetabular prosthesis during a revision orthopedic surgical procedure. This will, in turn, provide more surgical flexibility during implantation of the acetabular prosthesis, provide the surgeon with a variety of surgical options at the time of the surgical procedure, provide a universal acetabular cup that can be configured for use in many circumstances, reduce hospital inventory and inventory tracking requirements, and reduce the overall surgical time, cost and complexity. It is, therefore, an object of the present invention to provide such a method and apparatus for providing a metal-metal constrained liner that may have the articulating bearing surface altered without requiring removal of the acetabular prosthesis.

SUMMARY OF THE INVENTION

In accordance with the teachings of the present invention, a method and apparatus for providing an acetabular prosthesis that includes a metal-metal constrained liner having a modular bearing component for use in orthopedic surgery is disclosed. The acetabular prosthesis includes a metal-metal bearing surface. The acetabular prosthesis further includes a mechanism for fixing a second bearing surface within the acetabular prosthesis. In this regard, a surgeon performing a revision surgery can select the appropriate modular attachment components depending on the patient's needs, thereby providing a versatile acetabular prosthesis.

In one embodiment, an acetabular prosthesis for implantation in an acetabulum is provided. The acetabular prosthesis includes a modular constraint component. The acetabular prosthesis has an outer surface, which is operable to be received in the acetabulum and an inner surface, which is operable as a metal bearing. The modular constraint component has an attachment member and an engagement member, which enables its attachment to the acetabular prosthesis.

In another embodiment, an acetabular prosthesis for implantation in an acetabulum includes a modular bearing insert. The acetabular prosthesis has an outer surface, which is operable to be received in the acetabulum and an inner surface, which is operable to receive the modular bearing insert having a second bearing surface that is generally used during a revision surgery.

In yet another embodiment, an acetabular prosthesis for implantation in an acetabulum includes a modular bearing insert having an integral constraint component. The acetabular prosthesis has an outer surface, which is operable to be received in the acetabulum and an inner bearing surface, which is operable to receive the modular bearing insert having the integral constraint component. The modular bearing insert having the integral constraint component is secured to the acetabular prosthesis by way of a locking ring that is operable to be slidably received in a channel formed in the acetabular prosthesis.

In yet another embodiment, an acetabular prosthesis for implantation in an acetabulum includes a floating bearing insert. The acetabular prosthesis has an inner metal bearing surface, which is operable to receive the floating modular bearing insert. A constraining ring is used to hold the modular bearing insert onto the acetabular prosthesis while constraining movement of the femoral implant.

In still another embodiment, a method for implanting an acetabular prosthesis having a modular bearing component in the acetabulum is provided. This method includes providing an acetabular prosthesis that has an outer surface and an inner bearing surface. Engaging the outer surface of the acetabular prosthesis with a surgically prepared portion of the acetabulum. A head portion from a femoral prosthesis is then coupled to the inner bearing surface of the acetabular prosthesis. To perform a revision, the femoral head is removed from the acetabular prosthesis and a bearing insert is disposed on the inner bearing surface of the acetabular prosthesis. A new femoral head is then coupled to the femoral prosthesis, which corresponds to the size of the bearing surface of the insert.

Use of the present invention provides a method and apparatus for providing an acetabular prosthesis that includes a metal-metal constrained liner further having a modular bearing component for use generally during a revision orthopedic surgical procedure. As a result, the aforementioned disadvantages associated with the currently available acetabular prosthesis have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is a perspective view of an acetabular prosthesis according to the teachings of a first embodiment of the present invention;

FIG. 1A is a perspective view of an acetabular prosthesis according to the teachings of a second embodiment of the present invention;

FIGS. 1B and 1C represent top and side views of the second embodiment of the present invention;

FIGS. 9-12 depict the insertion of the acetabular prosthesis and femoral components according to the teachings of the present invention;

FIG. 26 represents a constraining ring according to the teachings of another embodiment of the present invention;

FIG. 27 represents a locking ring according to the teachings of the present invention;

FIG. 28 represents an assembled prosthetic according to the teachings of the present invention;

FIGS. 29A, 29B, and 30 represent an alternate acetabular prosthetic;

FIGS. 31A, 31B, and 32 represent yet another embodiment of the present invention;

FIGS. 38A, 38B, and 38C represent an alternate constraining ring design; and

DETAILED DESCRIPTION OF THE PREFERRED EMBODIMENTS

Figure 2:
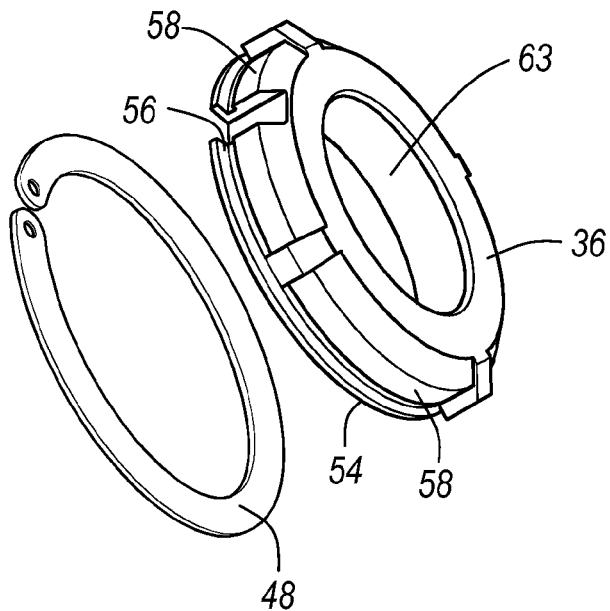
FIG. 2 is a perspective view of a constraining ring with locking ring.

The following description of the preferred embodiments are merely exemplary in nature and are in no way intended to limit the invention, its application, or uses.

Referring to FIG. 1, an acetabular prosthesis 20 according to the teachings of a first embodiment of the present invention is shown. The acetabular prosthesis 20 has a inner surface 22 defining a first metal bearing surface 24 and an outer surface 26 capable of being coupled or impacted into a prepared acetabulum 28. Defined between the outer surface 26 and the inner surface 22 is a peripheral surface or rim 30. Disposed on the peripheral surface 30 is a locking mechanism 34. The locking mechanism 34 is capable of coupling a second prosthetic such as an optional constraining ring 36 (see FIG. 2), or an optional insert bearing 38 (see FIG. 4) into a bearing cavity 40 which is defined by the inner surface 22 of the acetabular prosthesis 20. The second prosthetic substantially surrounds a head of a femoral component (as further described later), were substantially encloses includes for example a slotted constraining ring.

The outer surface 26 of the acetabular prosthesis 20 defines a plurality of locking projections 42 for coupling the acetabular prosthesis 20 to the prepared acetabulum 28. It is envisioned that the outer surface 26 can be surface treated to facilitate bone ingrowth or fixation to bone cement, such as by porous coating.

FIG. 1A illustrates an alternate embodiment of the acetabular prosthesis 120, which is similar to the acetabular prosthesis 20, except it has a plurality of through holes 44 to assist in fixation to the prepared acetabulum 28 (see FIG. 6). Defined in the peripheral surface 30 is the plurality of through holes 44 for mounting the acetabular prosthesis 120 to the prepared acetabulum 28 using standard bone coupling fasteners or screws 43 (shown in FIG. 14).

FIGS. 1B and 1C represent top and side views, respectively, of the acetabular prosthesis 120 of FIG. 1A. Although there are many ways to couple the constraining ring 36 or insert bearing 38 into the bearing cavity 40 defined by the inner surface 22 such as fasteners or tabs, shown is the locking mechanism 34 is formed by a locking flange 35 which defines a coupling groove 46. The coupling groove 46 is designed to accept a locking ring 48 (shown in FIG. 2). The locking flange 35 has a plurality of alignment notches 50 disposed therein to facilitate the acceptance of the locking ring 48 and alignment of the acetabular prosthesis 120, further discussed herein.

Figure 2B:
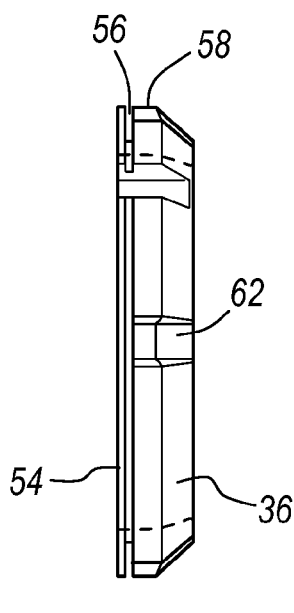
FIGS. 2A and 2B represent top and side views of the constraining ring according to the teachings of the present invention.
Figure 2A:
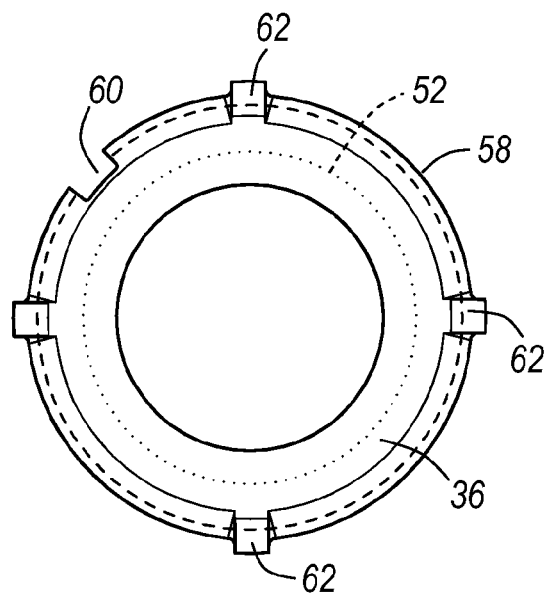

FIGS. 2 through 2B depict the optional constraining ring 36. The constraining ring 36 is preferably made of any material softer than the implant material such as a polymer material like UHMWPE and may be reinforced with a metal or polymer reinforcement 52. The constraining ring 36 has a lower surface 54 which mates with the peripheral surface 30 of the acetabular prosthesis 20. Immediately adjacent to the lower surface 54 is a constraining ring groove 56 defined in a constraining ring outer surface 58. The constraining ring groove 56 is used to couple the constraining ring 36 to the acetabular prosthesis 120, via the locking ring 48. The constraining ring outer surface 58 defines a constraining ring alignment notch 60, which corresponds to the alignment notch 50, in the acetabular prosthesis 120 (see FIG. 1A). The notches 50 and 60 are used to gain access to the locking ring 48 by a tool (not shown) that engages and disengages the locking ring 48 by way of the pair of holes 51 or other means in the locking ring 48 (see FIG. 2). Further disposed on the constraining ring outer surface 58 is a plurality of ring flanges 62 which are used to rotationally position the constraining ring 36 about the acetabular prosthesis 20 to allow for alignment of the notches 50 and 60. The constraining ring 36 further has a generally concave constraining ring bearing surface 63 which encapsulates a first head 67 of a femoral prosthesis 68 to prevent dislocation of the joint (see FIG. 10).

Figure 3:
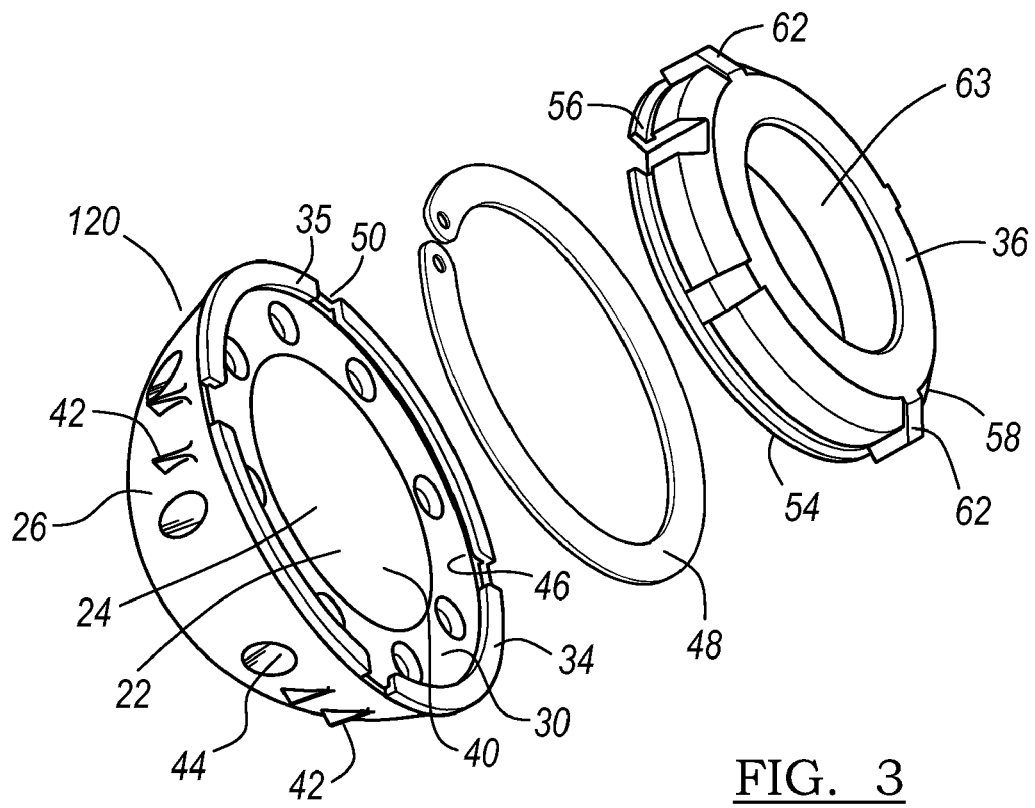
FIG. 3 is a perspective view of the acetabular prosthesis of FIG. 2 with a constraining ring.
Figure 3A:
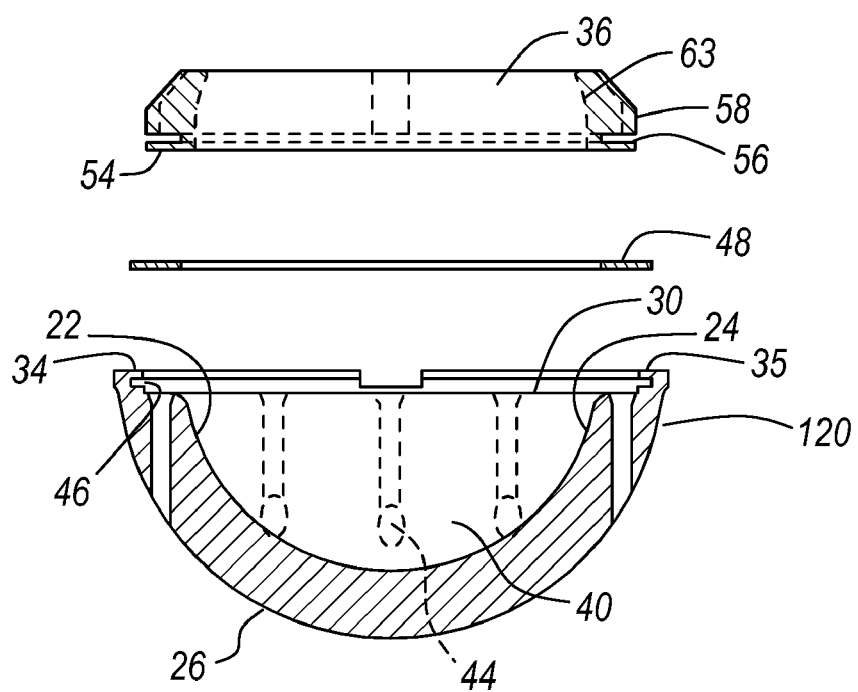
FIG. 3A is a side view of the acetabular prosthesis and constraining ring of FIG. 3.

FIGS. 3 and 3A depict the relational views of the optional constraining ring 36, locking ring 48, and acetabular prosthesis 120. It is envisioned that the locking ring 48 be initially expanded and disposed in the constraining ring groove 56 of the constraining ring outer surface 58. After alignment of the constraining ring alignment notch 60 with one of the alignment notches 50 of the acetabular prosthesis 120, the locking ring 48 is contracted to allow its incorporation under the locking flange 35 into the coupling groove 46. This couples the lower surface 54 of the constraining ring 36 to the peripheral surface or rim 30 of the acetabular prosthesis 120.

Figure 4:
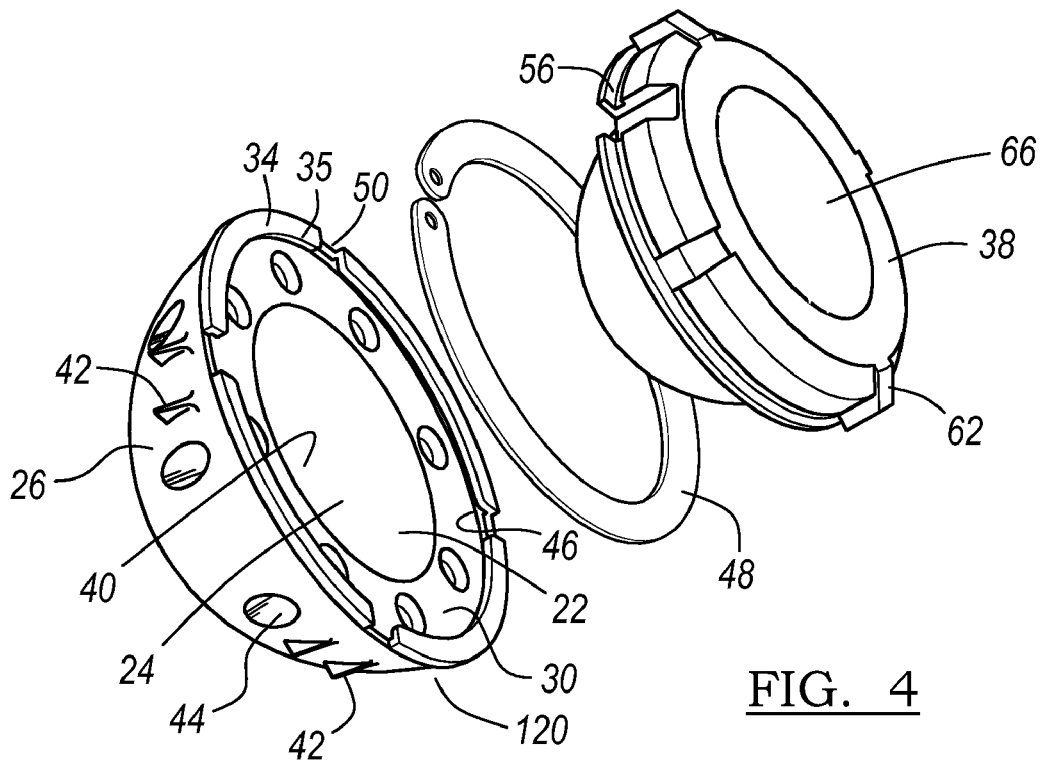
FIG. 4 is a second perspective view of an acetabular prosthesis of FIG. 2 with a modular bearing component.
Figure 4A:
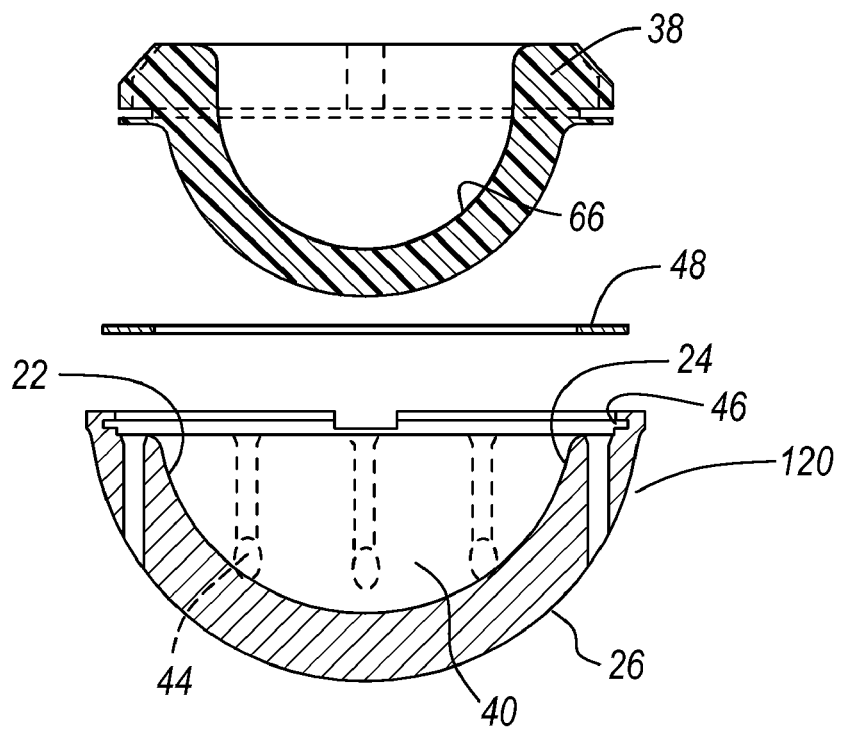
FIG. 4A is a side view of the acetabular prosthesis of FIG. 4.

FIGS. 4 and 4A depict the acetabular prosthesis 120 of FIG. 1A with the insert bearing 38. The insert bearing 38 is shown with the locking ring 48. It is envisioned, however, that other locking mechanisms such as screws, snaps, and locking flanges can be used to restrain the insert bearing 38 to the acetabular prosthesis 120.

The insert bearing 38 defines a concave bearing surface 66. The bearing surface 66 has an interior diameter that is smaller than the interior diameter of the inner surface 22 of the acetabular prosthesis 120. For example, the inner surface 22 of the acetabular prosthesis 120 may have a radius of about 32 mm, while the bearing surface 66 of the insert bearing 38 may have an inner radius of about 28 mm. The difference in depth between the first metal bearing surface 24 of the acetabular prosthesis 120 and the bearing surface 66 allows for the proper functioning of a revision joint assembly. In this regard, should it be desired to change from a metal-metal articulating bearing surface to a poly-metal articulating bearing surface, the surgeon may simply insert the insert bearing 38. Those skilled in the art would recognize that the insert bearing 38 can have an elevated wall, plus five, 10 degree, high wall etc, and be formed of bio-compatible metals, ceramics, or polymers such as UHMWPE.

Figure 5:
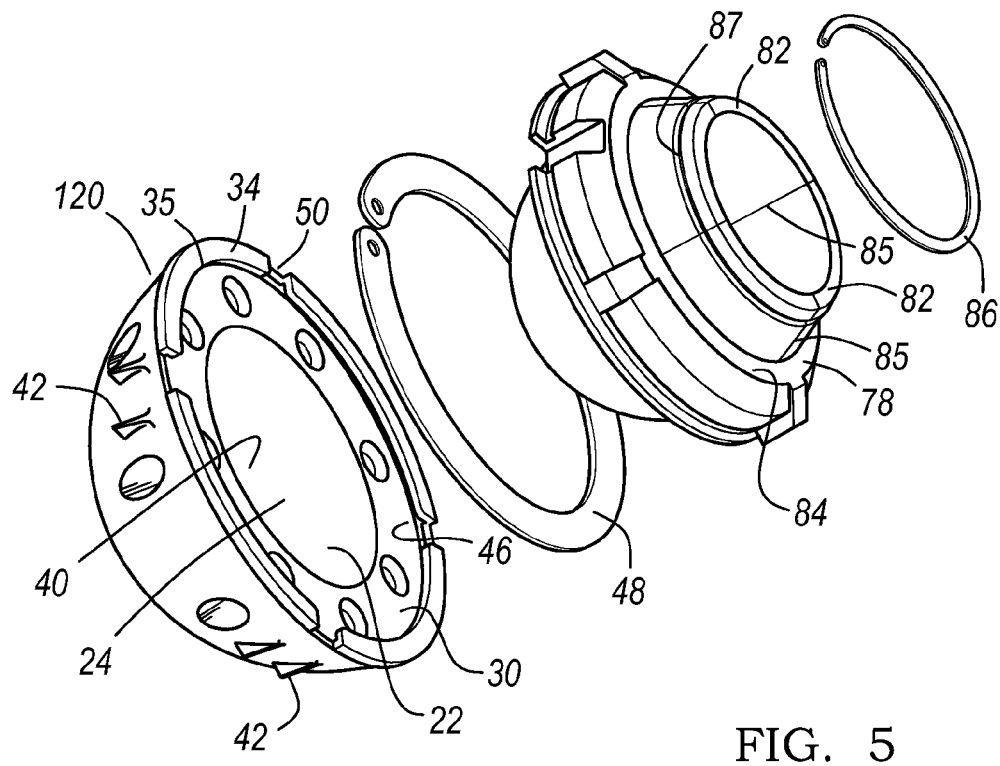
FIG. 5 is a perspective view of the acetabular prosthesis of FIG. 2 with a modular constraining bearing component.
Figure 5A:
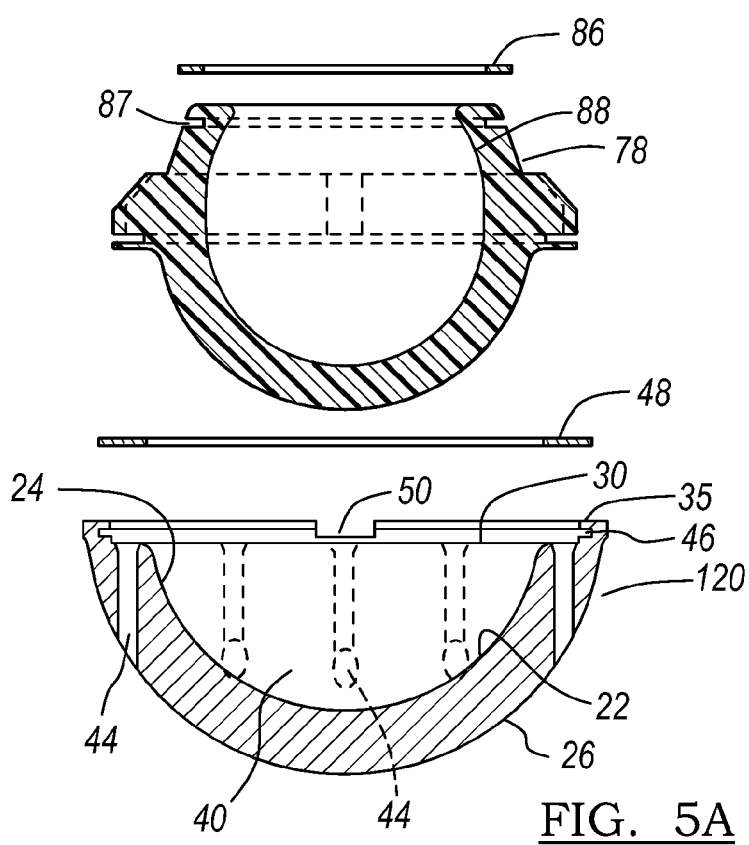
FIG. 5A is a side view of the acetabular prosthesis of FIG. 5.

FIGS. 5 and 5A depict the use of a constrained bearing liner 78. The constrained bearing liner 78 functions to constrain a second modular head 80 of a femoral prosthesis 68 (shown in FIG. 21). The constrained bearing liner 78 has a plurality of built in constraining members 82. These constraining members 82 are disposed about an upper surface 84 of the constrained bearing liner 78 and are separated by a plurality of slits 85 or the like. The constrained bearing liner 78 is coupled to the acetabular prosthesis 120 by the locking mechanism 34 described previously. In addition, the constrained bearing liner 78 has a second locking ring 86 which is placed into a second groove 87 disposed within the constraining members 82. The second locking ring 86 functions to close the constrained bearing liner 78 about the second modular head 80. As can be seen in FIG. 5A, which depicts an exploded cross-section of this embodiment, the constrained bearing liner 78 defines an constrained bearing interior surface 88. The constrained bearing interior surface 88 substantially encapsulates the second modular head 80 of the femoral prosthesis 68 (see FIG. 21).

Figure 6A:
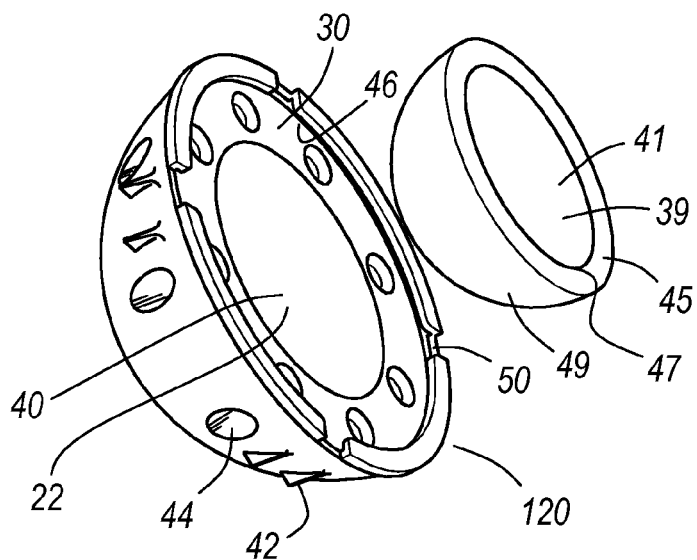
FIGS. 6A and 6B are perspective views of another embodiment of the present invention.
Figure 6B:
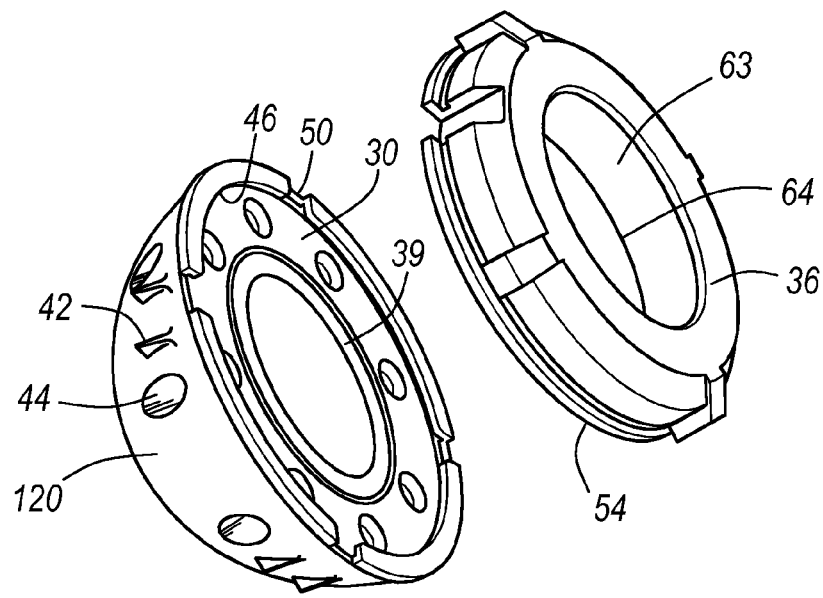

FIGS. 6A and 6B depict the use of a modular bearing liner 39. The modular bearing liner 39 is disposed within the bearing cavity 40 of the acetabular prosthesis 120. The modular bearing liner 39 has an inner bearing surface 41 which forms an articulating joint with the second head 80 of the femoral prosthesis 68. The modular bearing liner 39 also has an exterior surface 49 which mates to the inner surface 22 of the acetabular prosthesis 120. Defined between the outer surface 49 and the inner bearing surface 41 is a bearing peripheral surface 45. As best seen in FIG. 6B, when the modular bearing liner 39 is disposed within the bearing cavity 40, the modular bearing peripheral surface 45 is coplanar with the upper peripheral surface 30 of the acetabular prosthesis 120. Both the upper peripheral surface 30 and the bearing liner peripheral surface 39 mate with the lower surface 54 of the constraining ring 36. The line 47 defined between the constraining ring bearing surface 63 and the lower surface 54 of the constraining ring 36 mates with the line 64 defined between the liner bearing peripheral surface 45 and the liner inner surface 41. This allows for the proper encapsulation of the second modular head 80.

Figure 7A:
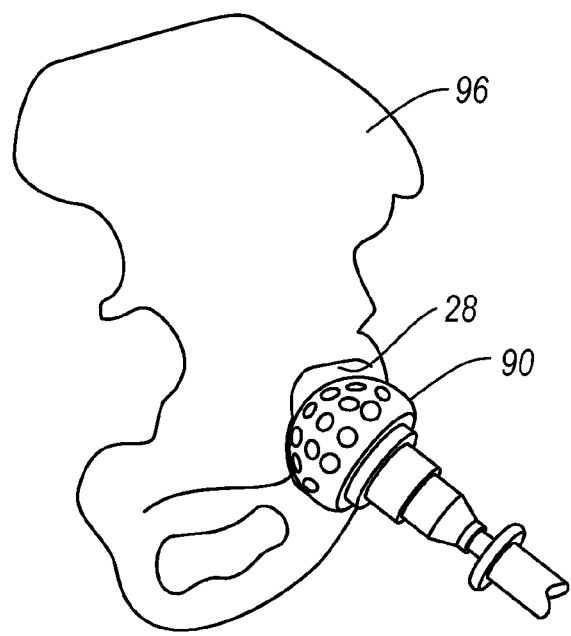
FIGS. 7A-8 depict the resection of the acetabular portion according to the teachings of the present invention.
Figure 7B:
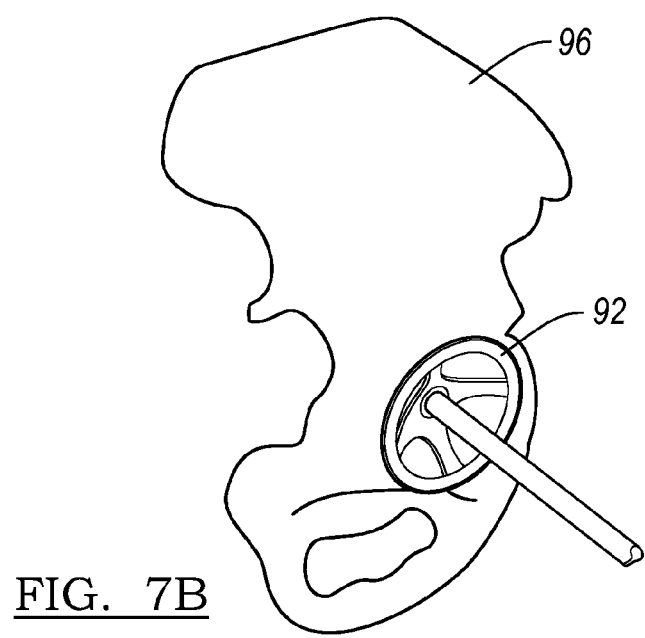

FIGS. 7A and 7B disclose the method of preparing the pelvis 96. After the natural femoral head (not shown) has been dislocated from the pelvis 96, a bore 90 is used to enlarge the acetabular cavity 94 for acceptance of the acetabular prosthesis 120. An acetabular trial gauge 92 is used to determine the reaming accuracy and to determine the exterior diameter of the acetabular prosthesis 120 to be used.

Figure 8:
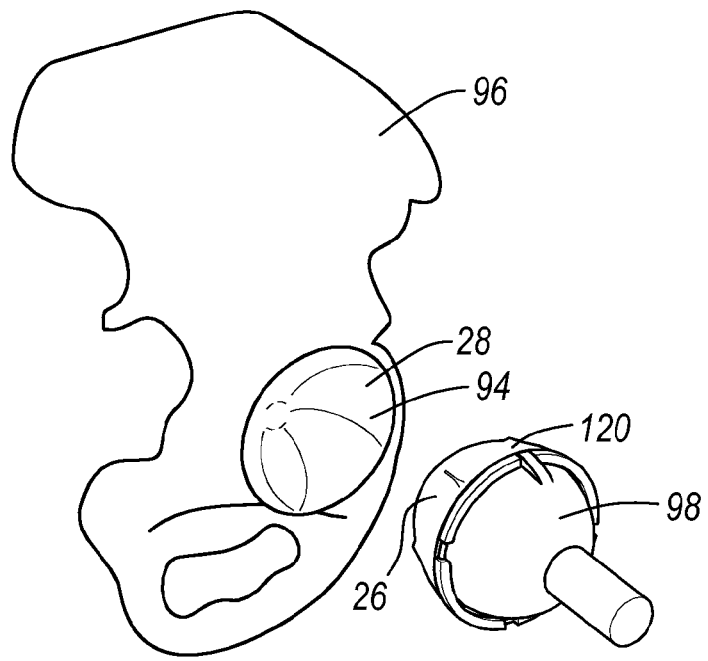
Figure 9:
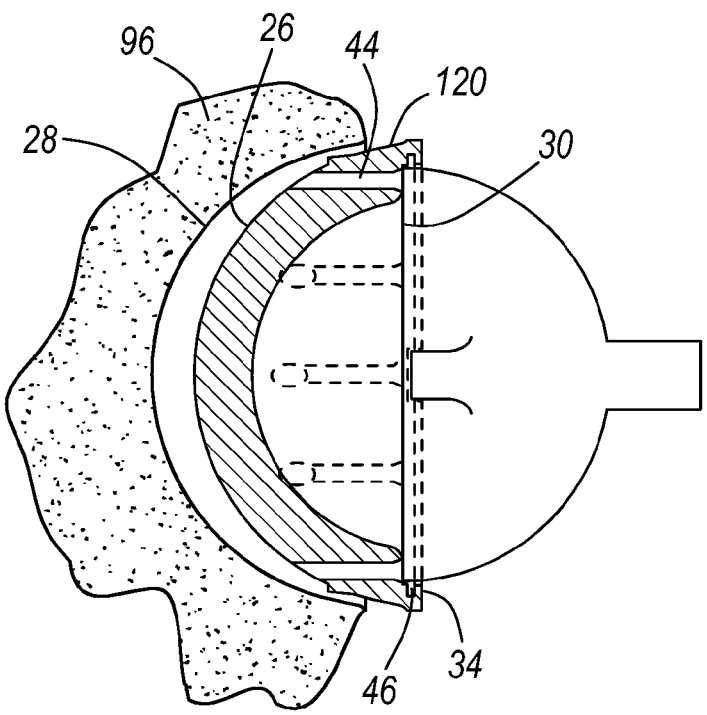

FIGS. 8 and 9 depict the insertion of the acetabular prosthesis 120 into the prepared acetabulum 28. It is envisioned that the acetabular prosthesis 120 will be aligned by using either the fixation holes 44 or the alignment notches 50 disposed on the peripheral surface or rim 30. The acetabular prosthesis 120 will then be impacted along the upper peripheral surface 30 by the use of an impacting tool 98. After being positioned, the acetabular prosthesis 120 can be fixed using bone coupling fasteners or screws 43 or bone cement to set the acetabular prosthesis 120 into the prepared acetabulum 28.

FIGS. 10 through 12 illustrate the insertion of the head 67 of a femoral prosthesis 68 into the acetabular prosthesis 120, along with the use of the optional constraining ring 36. It should again be noted that as the inner surface 22 of the acetabular prosthesis 120 is a highly polished metal bearing surface formed from a bio-compatible material such as titanium, cobalt chrome, stainless steel, etc. The first head 67 of the femoral prosthesis 68 will articulate within the bearing cavity 40 defined by the inner surface 22 of the acetabular prosthesis 120. As can be seen, the first head 67 is inserted into the bearing cavity 40. Next, the constraining ring 36, which was previously disposed about the neck 102 of the femoral implant 68, is positioned adjacent to the peripheral surface 30 of the acetabular prosthesis 120. The locking ring 48 is inserted into the coupling groove 46 defined by the locking flange 35 and the constraining ring 36 is released to affix the constraining ring 36 onto the acetabular prosthesis 120. In this way, a metal-metal articulating bearing surface is formed between the inner surface 22 and the femoral head 67.

Figure 13:
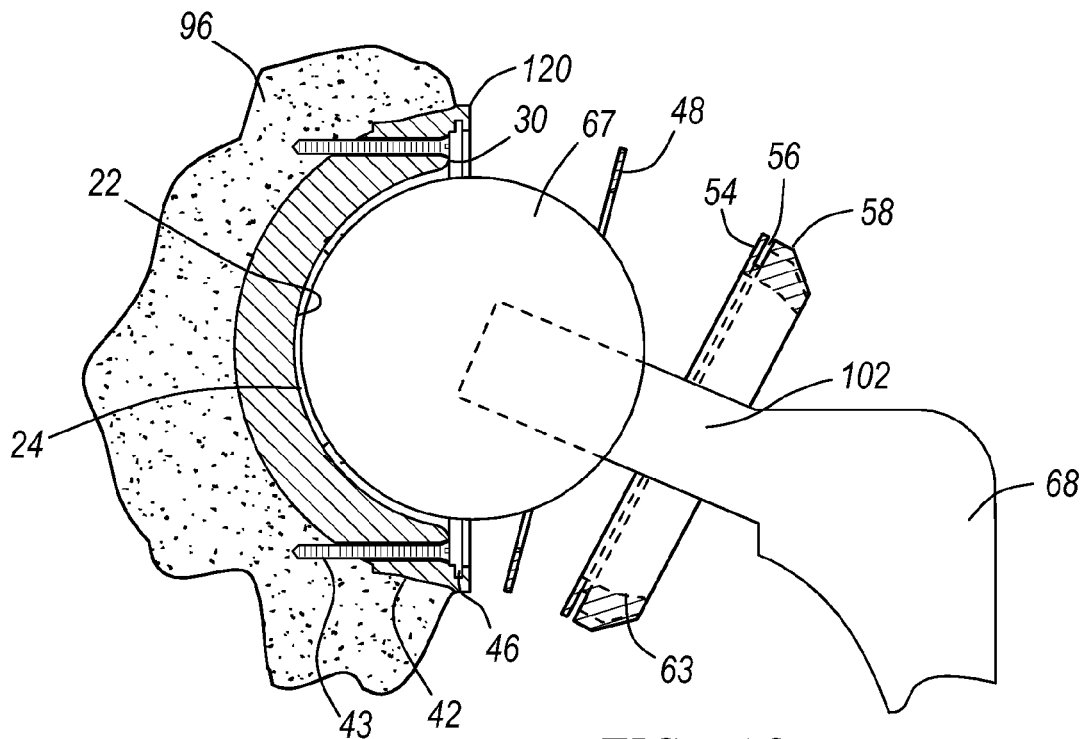
FIGS. 13-14 depict a cross-sectional view of the insertion of a femoral prosthesis into the acetabular prosthesis according to the teachings of the present invention.
Figure 14:
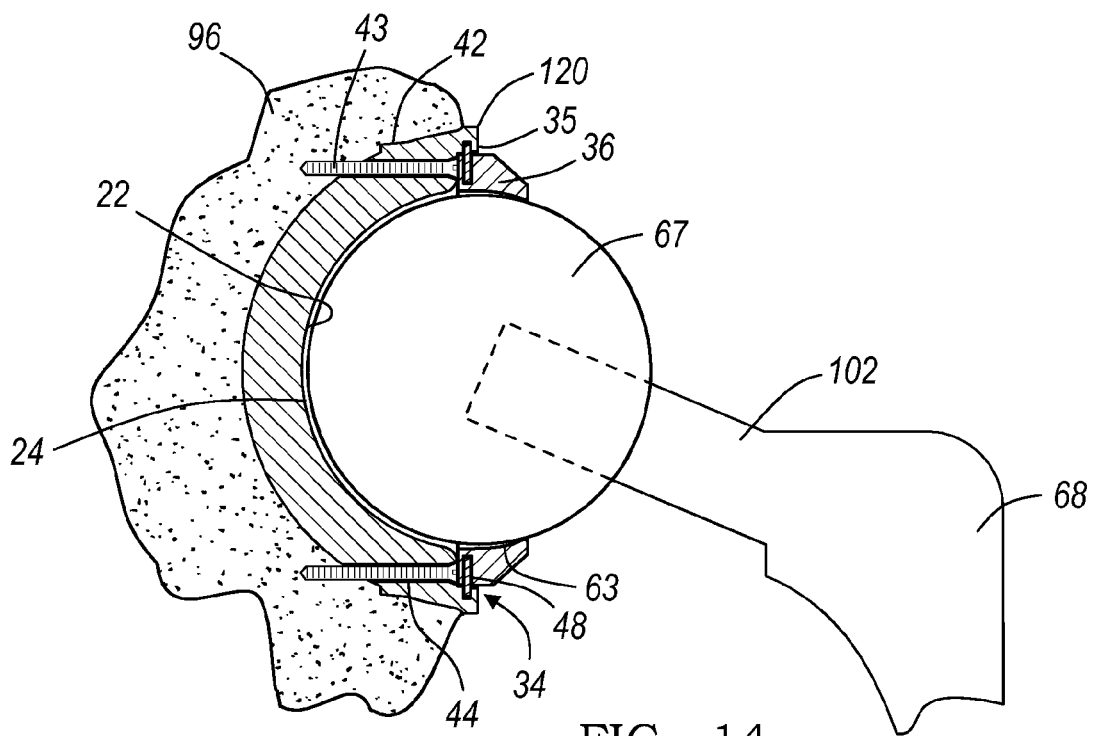

FIGS. 13 and 14 show cross-sections of the insertion of the first head 67 into the acetabular prosthesis 120. As is show, the first femoral head 67 engages the metal bearing surface 24. The locking ring 48 is positioned within the constraining ring groove 56 to fix the constraining ring 36 to the acetabular prosthesis 120, thus locking the first head 67 into its proper orientation. FIG. 14 depicts the location of the locking ring 48 with respect to the acetabular prosthesis 120 and constraining ring 36. Further shown is the location of the fastener or screw 43 to the locking mechanism 34.

Figure 15:
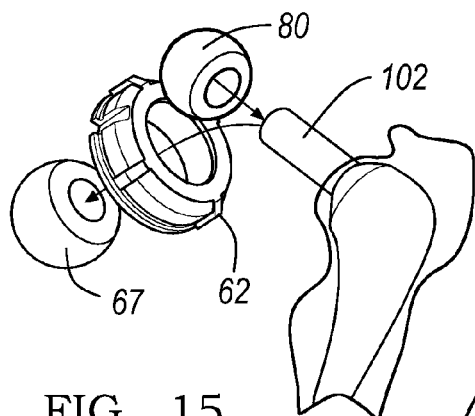
FIGS. 15-19 depict the revision of the joint.

As is known, occasionally bearing surfaces may wear out or the stability of the joint is unacceptable, and a revision operation may then take place. FIGS. 15 through 19 show the removal of the femoral prosthesis 68 during a revision surgery. The femoral prosthesis 68 is optionally the same prosthetic 68, which was inserted in FIGS. 11 and 12. FIG. 15 depicts the removal of the first head 67 and its replacement with the second modular head 80. It is envisioned that the first head 67 or second head 80 can be formed of metal or ceramic or combinations thereof. Should the optional constraining ring 36 be used, it must be removed during the revision. The method of removing the constraining ring 36 is the opposite of the steps as those described above for its insertion.

Figure 16:
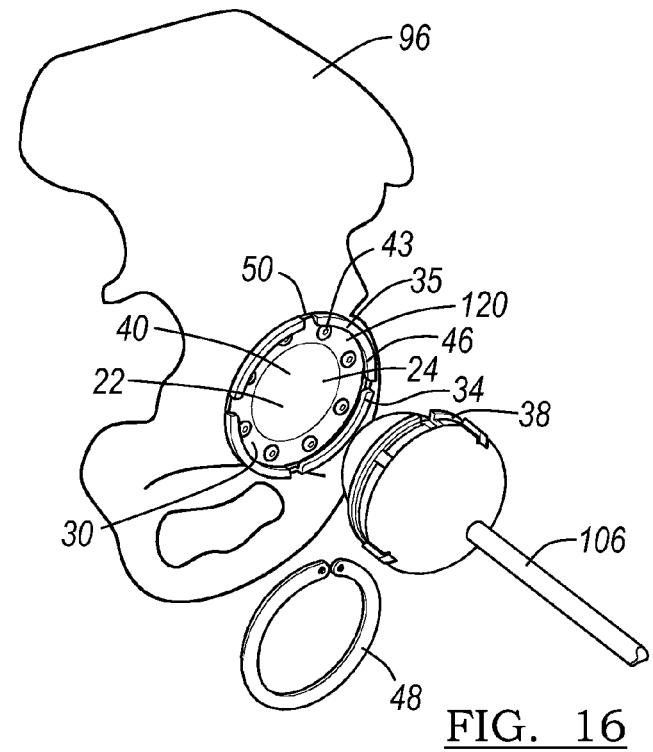
Figure 17:
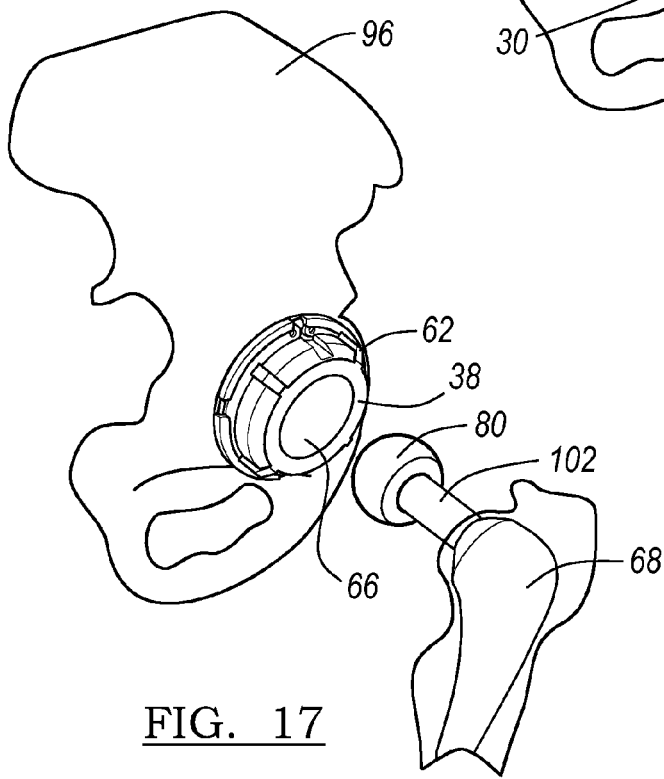

FIGS. 15 through 17 depict the insertion of the insert bearing 38. First, the first head 67 of the femoral prosthesis 68 must be modified so it can be accepted into the insert bearing 38. The first head 67 of the femoral prosthesis 68 must be removed from the neck 102. A smaller second modular head 80, typically a 28 millimeter ball, is then inserted onto the neck 102 of the femoral prosthesis 68. The insert bearing 38 is then inserted into the bearing cavity 40 of the acetabular prosthesis 120. As it is important not to deform the inner bearing surface 66 of the insert bearing 38, a tool 106 is used which loads the exterior of the insert bearing 38. The insert bearing 38 is pressed into the acetabular prosthesis 120 and locked into place using the locking ring 48.

Figure 18:
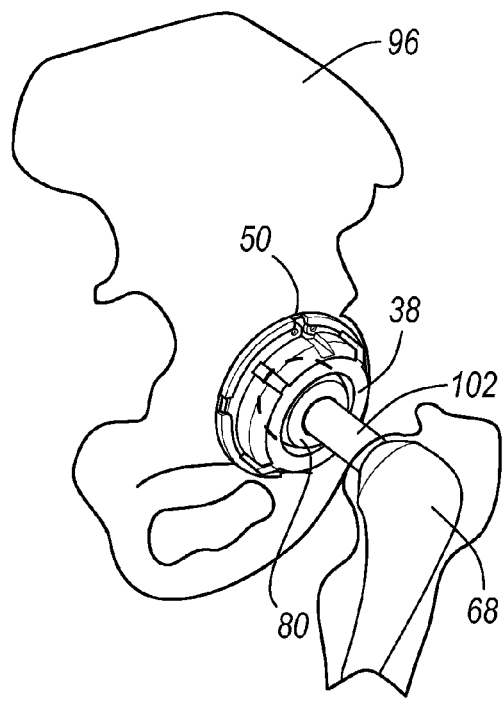
Figure 19:
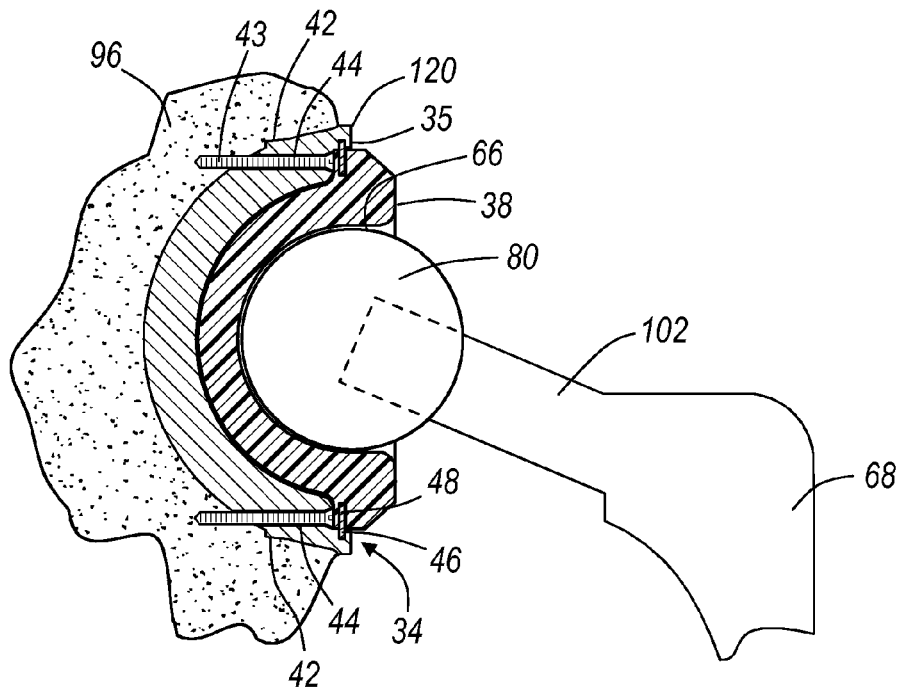

FIGS. 18 and 19 depict the second modular head 80 of the femoral prosthesis 68 positioned within the insert bearing 38. As is shown, the insert bearing 38 is of the "non-constrained type" which allows for maximum joint articulation. Moreover, it should be noted that a poly-metal articulating bearing surface is formed between bearing surface 66 and femoral head 80.

Figure 20:
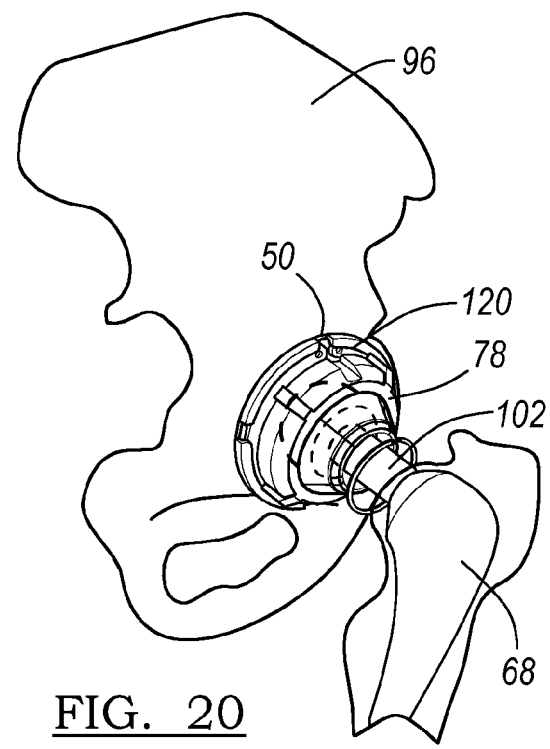
FIGS. 20-21 depict the insertion of a femoral component into an acetabular prosthesis utilizing the constraining bearing depicted in FIGS. 5 and 5A.
Figure 21:
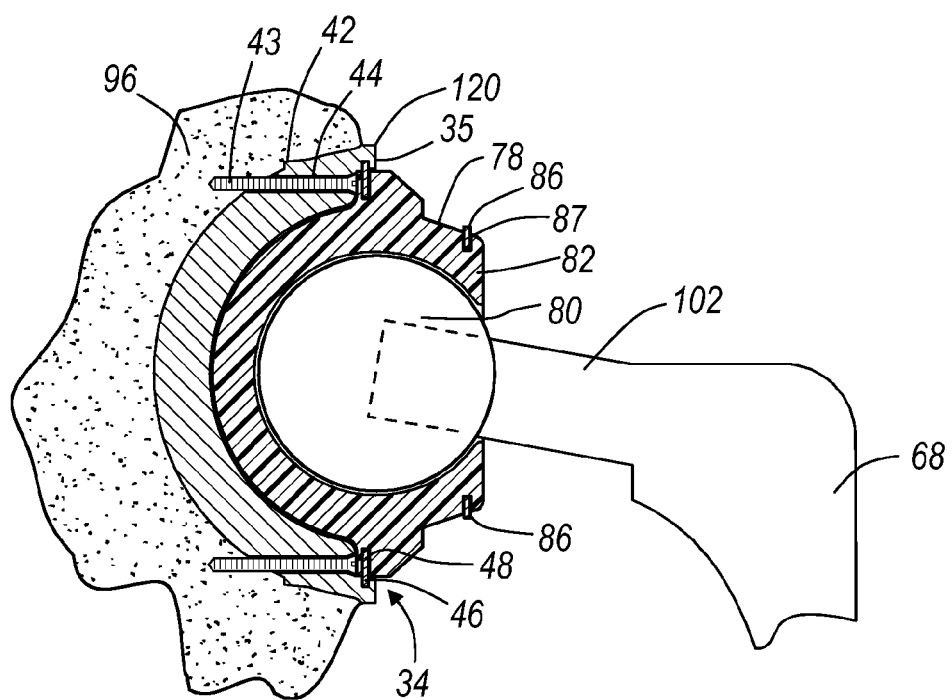

FIGS. 20 and 21 depict the use of the constrained bearing liner 78. The constrained bearing liner 78 is inserted in a fashion similar to that described above. Additionally, however, the second locking ring 86 is used to compress the constraining members 82 of the constrained bearing liner 78 about the second modular head 80 of the femoral prosthesis 68. Here again, a poly-metal articulating bearing surface is formed between bearing interior surface 88 and modular head 80.

Figure 22:
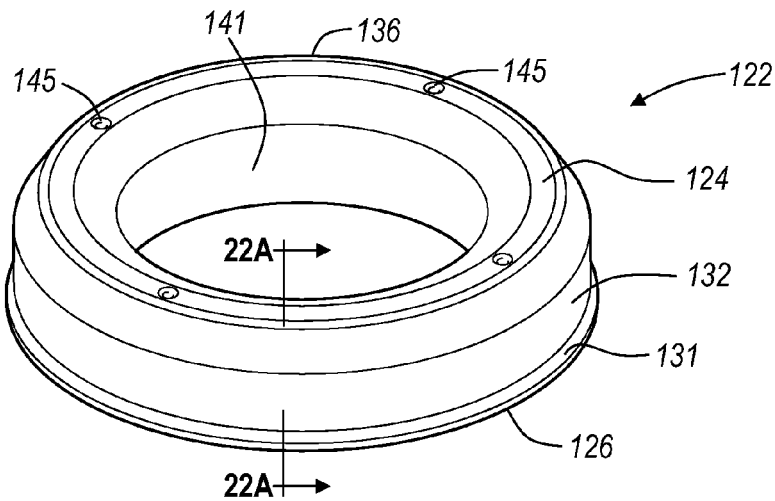
FIG. 22 represents an alternate constraining ring according to the teachings of the present invention.

FIG. 22 depicts the optional constraining ring 122. The constraining ring 122 is preferably made of any material softer than the implant material such as a polymer material like UHMWPE and is reinforced with a metal or polymer reinforcement ring 124. The constraining ring 122 has a lower surface 126 which mates with the peripheral surface 128 of the acetabular prosthesis 128. Immediately adjacent to the lower surface 126 is a constraining ring groove 131 defined in constraining ring outer surface 132. The constraining ring groove 131 is used to couple the constraining ring 122 to the acetabular prosthesis 128, via the locking ring 134.

Figure 22A:
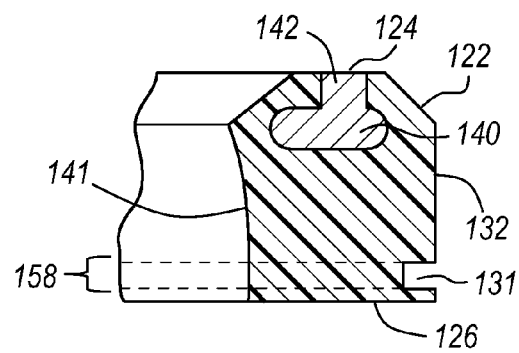
FIG. 22A represents a cross sectional view of the constraining ring shown in FIG. 22.
Figure 23:
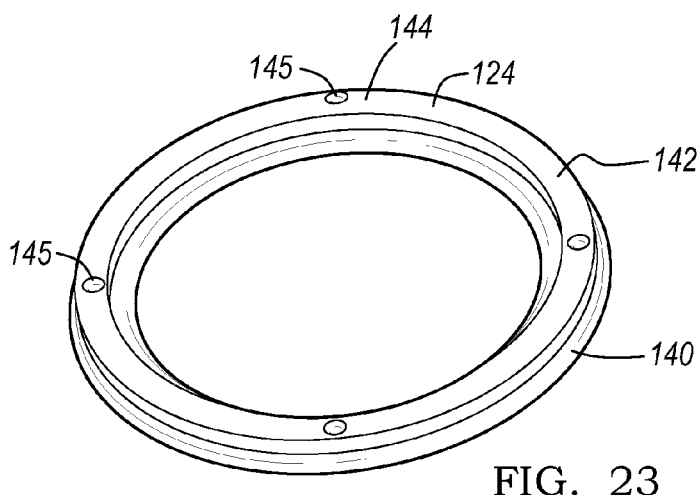
FIG. 23 represents an optional reinforcement ring shown in FIG. 22A.

Defined on a top surface 136 of constraining ring 132 is the reinforcement ring 124. As be seen in FIGS. 22A and 23, the reinforcement ring 124 is integrally molded within the constraining ring 122. The reinforcement ring 124 has a base ring 140 and interface ring 142, which is aligned with the top surface of constraining ring 122. The cross-section of reinforcement ring 124 is configured to mechanically interlock with the polymer of constraining ring 122. Defined by the top surface 144 of the reinforcement ring 124 are a plurality of alignment depressions 145, which are used during the molding process to align the reinforcement ring 124 within an injection mold (not shown) used to form the constraining ring 122. It should again be noted that the reinforcement ring 124 is a bio-compatible material such as titanium, cobalt chrome, stainless steel, etc. It is envisioned that the reinforcement ring 124 can be formed of other biocompatible materials such as polymer or ceramics which have a stiffness greater then the stiffness of the material used to form the constraining ring 122.

Figure 24:
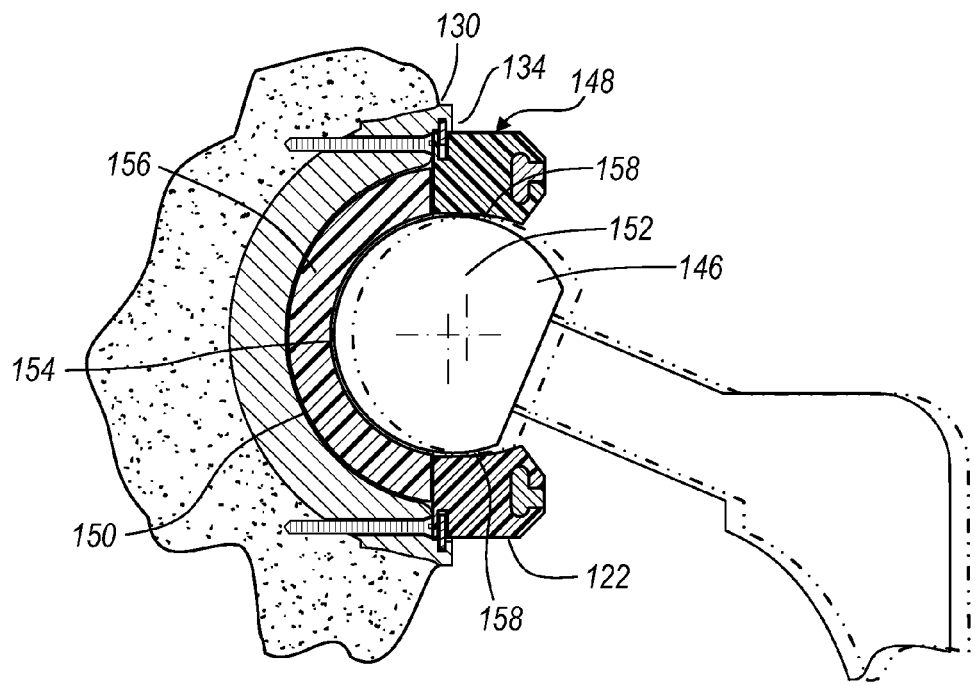
FIGS. 24 and 25 represents cross sectional views of a joint prosthetic according to the teachings of another embodiment of the present invention.

FIG. 24 shows a cross-section of the insertion of the first femoral head 146 into the acetabular prosthesis 148. As is shown, the first femoral head 146 engages the polymer insert bearing surface 150. The locking ring 134 is positioned within the constraining ring groove 130 to fix the constraining ring 122 to the acetabular prosthesis 148, thus locking the first femoral head 146 into its proper orientation.

The mating of the constraining ring 122 to the acetabular prosthesis 148 defines a generally capsule shaped cavity 152. The capsule shaped cavity 152 is formed from the generally spherical bearing surface 141 of the polymer insert bearing 156 and the partially spherical bearing surface 158 of the constraining ring 122. Disposed between the spherical bearing surfaces 154 and 153 is a generally flat 1 to 4 mm cylindrical portion 158.

During normal articulations of the acetabular joint during gate, the femoral head pulls away from the acetabular bearing surface from 1 to 4 mm. In the case of prosthetic joint 148 depicted in FIG. 24, the muscles associated with the prosthetic joint 148 will generally pull the first femoral head 146 into the polymer bearing surface 150. The generally capsule shaped cavity 152 however allows the first femoral head 146 to pull away from the acetabular bearing surface 154 from 1 to 4 mm (as shown in phantom), imitating the normal dynamics of a natural acetabular joint.

Figure 25:
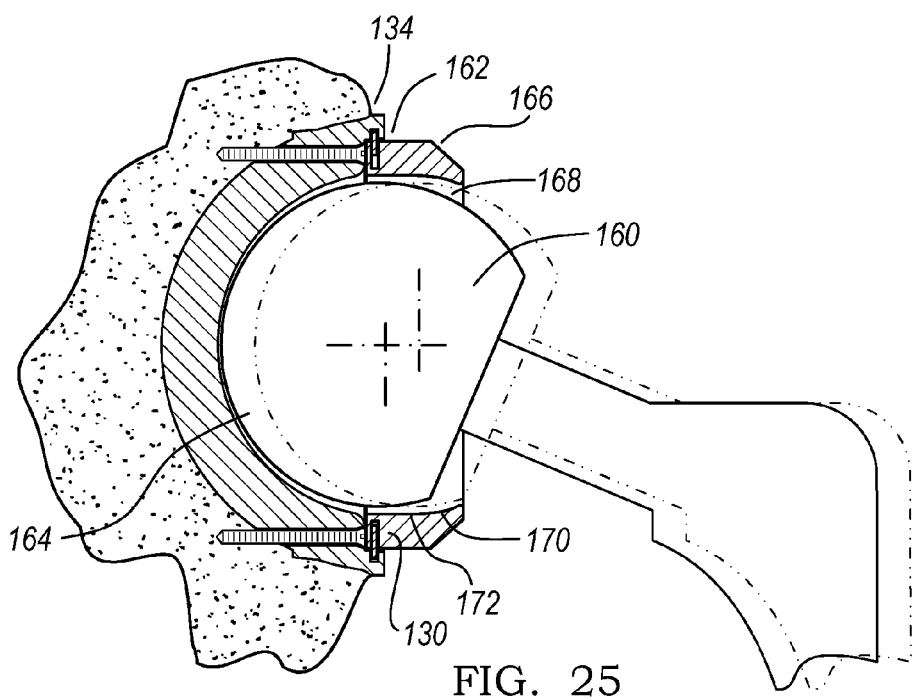

FIG. 25 shows a cross sectional view of the insert of a second femoral head 160 into the acetabular prosthesis 162. As is shown, the second femoral head 160 engages a metal bearing surface 164 of the acetabular prosthesis 162. The locking ring 134 is positioned within the constraining ring groove 130 to fix constraining ring 166 to the acetabular prosthesis 162, thus locking the second femoral head 146 into its proper orientation.

As described above, the mating of the constraining ring 166 to the acetabular prosthesis 162 defines a capsule shaped cavity 168. The capsule shaped cavity 168 is formed from the generally spherical bearing surface 164 of the acetabular prosthesis 162 and the partial spherical bearings surface 170 of constraining ring 166. Disposed between the spherical bearing surfaces 164 and 170 is 1 to 4 mm generally flat cylindrical portion 172. While the cylindrical portion 172 is shown defined in the constraining ring 166 it is equally envisioned that it can be formed on the acetabular prosthesis 162.

FIG. 26 represents a constraining ring 174 according to the teachings of the present invention. It is envisioned that the locking ring 176 can be expanded to be disposed within constraining ring groove 178. Formed on the locking ring 176 are a pair of inwardly directed flange 178, which are used to elastically deform the locking ring 176. The inwardly directed flanges 178 are positioned adjacent an elongated alignment notch 180 formed on the outer ring surface 182 of constraining ring 174.

FIG. 28 represents a perspective view of the assembled joint prosthesis. Shown is constraining ring 174 coupled to acetabular prosthesis 130 using locking ring 176. The elongated alignment notch 180 alloys for the surgeon to access the inwardly directed flanges 178 to facilitate removal of the constraining ring 174 as may be necessary in a reversionary surgery.

FIGS. 29A and 29B represent an acetabular prosthetic 200 according to the teachings of another embodiment of the invention. Shown is an acetabular cup 202 which is generally configured as the previous embodiments. The acetabular cup 202 defines a snap ring engagement groove 204 and a plurality of coupling through bores 206. Additionally defined by the acetabular cup 202 is at least one auxiliary alignment bore 208. The alignment bore 208 is configured to slidably accept an indexing flange 210 defined on an interface surface 212 of a constraining ring 214.

The constraining ring 214 has a cylindrical outer peripheral surface 216 which defines a snap ring engagement groove 218. Additionally defined in the outer periphery is an access notch 220 which allows access to the snap ring 222 to couple the constraining ring 214 to the acetabular cup 202. The constraining ring 214 additionally defines a first internal bearing surface 231 which is configured to slidably interface with a femoral prosthetic (not shown). Defined on the top surface 226 of the constraining ring 214 is a constraining lip 228 which is a projection 230 that defines an auxiliary constraining surface 232. The constraining lip 228 is radially disposed between 0° and 359° about a centerline C. The constraining lip 228 functions to provide additional constraining forces to reduce dislocation of the femoral prosthetic while allowing augmented joint movement when compared to a prosthetic having an augmented constraining surface which completely surrounds the constrained ring.

The use of the indexing flange 210 within the alignment bore 208 allows the physician to anatomically position the location of the constraining lip 228 with respect to any anatomical location, thus allowing a physician to engineer or adjust the articulation of the joint.

As shown in FIGS. 31A, 31B, and 32, the prosthetic 230 can have more than one constraining lip. Shown is a pair of constraining lips 232 and 234 which are shown being radially similar. It is envisioned, however, that the constraining lips 232 and 234 can have varying radial sizes $\theta_1$ $\theta_2$. These constraining lips 232 and 234 can either be evenly or unevenly distributed about the centerline C. Additionally, the constraining lips 232 and 234 can be of varying heights, $h_1$ and $h_2$, thus allowing for increased or decreased areas of the auxiliary bearing surfaces 235 and 237.

Figure 33:
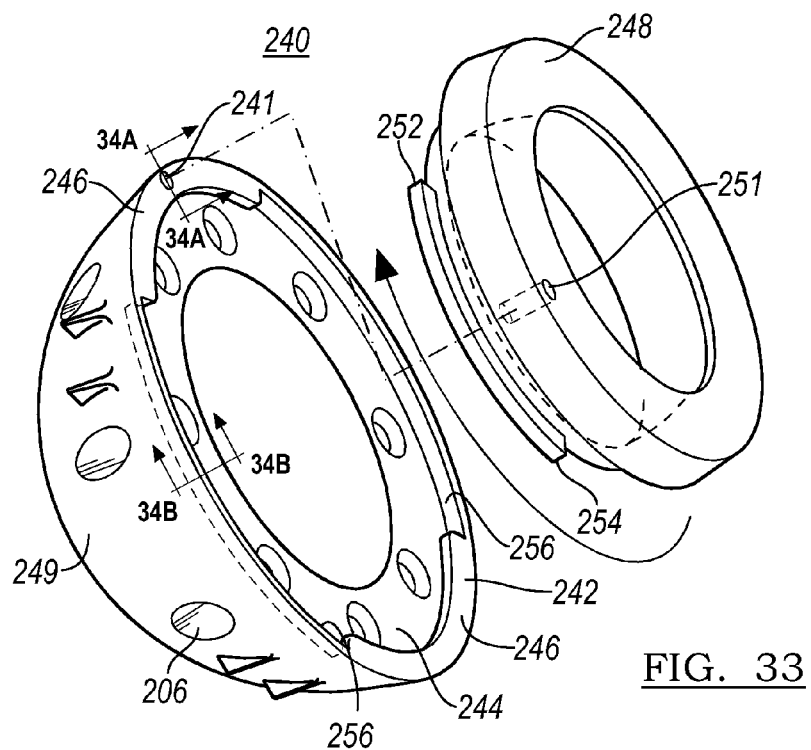
FIGS. 33, 34A and 34B represent an alternate coupling mechanism between the constraining ring and the acetabular prosthetic.

FIG. 33 represents an alternate prosthetic 240 having a modified coupling mechanism 242. The coupling mechanism 242 has a ring bearing surface 244 with a plurality of locking flanges or tabs 246 which are configured to lock a constraining ring 248 onto the ring bearing surface 244. As described below, defined in at least one of the locking flanges 246 is a constraining aperture 241. The constraining ring 248 has a locking mechanism 252 formed of a pair of locking flanges 254 which are configured to interweave with a pair of slots 256 defined by the locking flanges 246 of the acetabular cup. The locking flanges 254 are configured to be positioned below the locking flange 246 and rotated about the centerline to position the locking flanges 254 under the locking flange 246 of the acetabular cup 249.

Figure 34A:
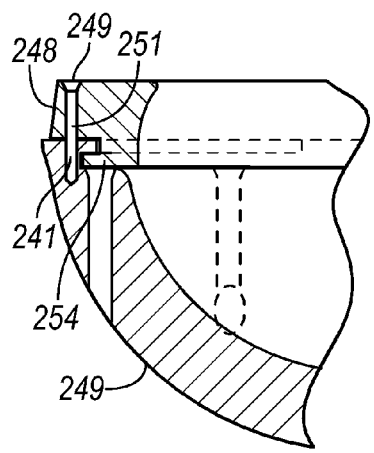
Figure 34B:
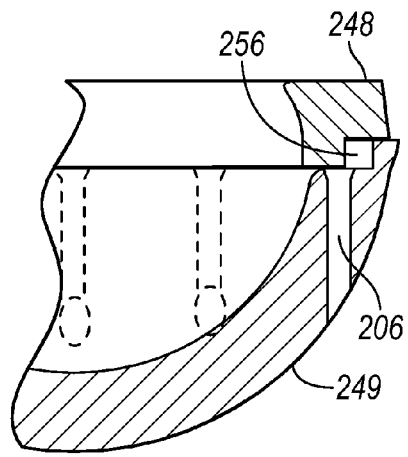

As best seen in FIG. 34A, the constraining ring 248 is rotated to a point where an alignment aperture 251 defined in the constraining ring 248 is aligned with the constraining aperture 241 of the acetabular cup. At this point, a pin or screw can optionally be placed through the apertures 241, 251 to rotationally lock the constraining ring 248 to the acetabular cup.

Figure 35A:
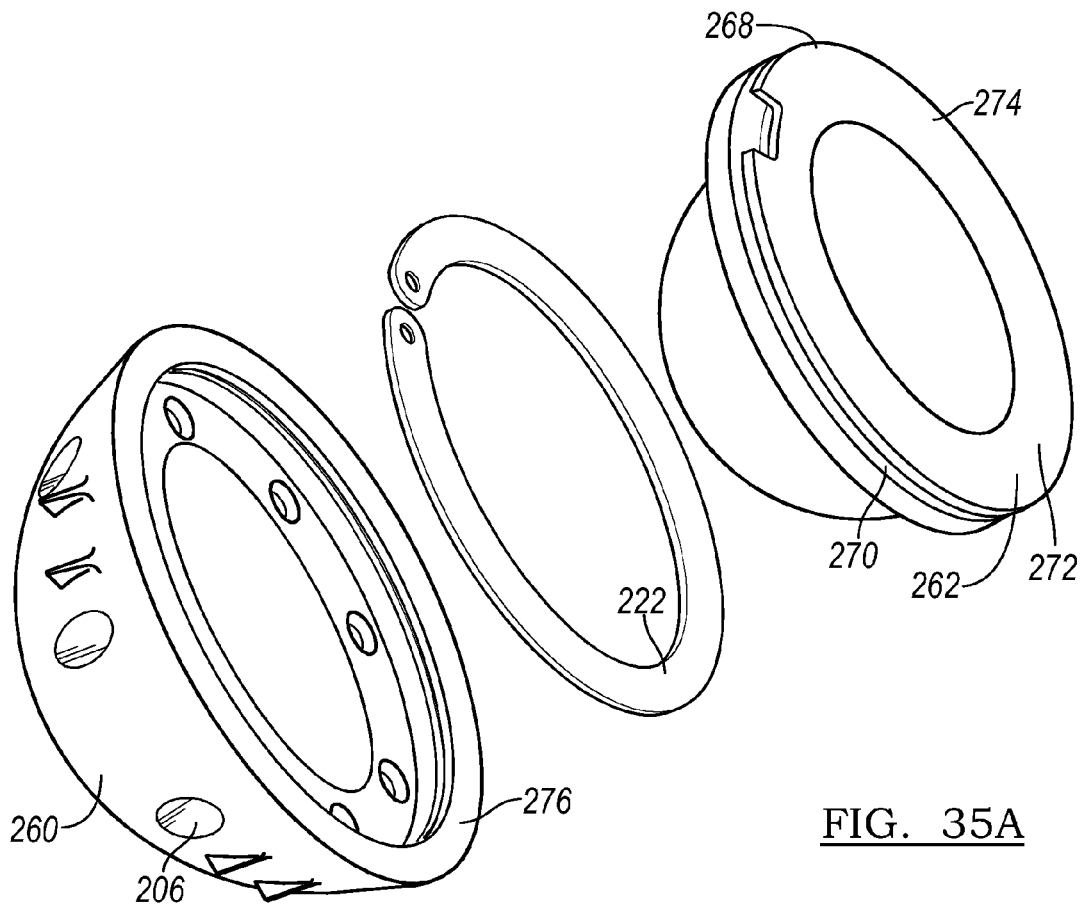
FIGS. 35A and 35B represent an alternate polymer bearing system coupled to an acetabular prosthetic of FIG. 1.
Figure 35B:
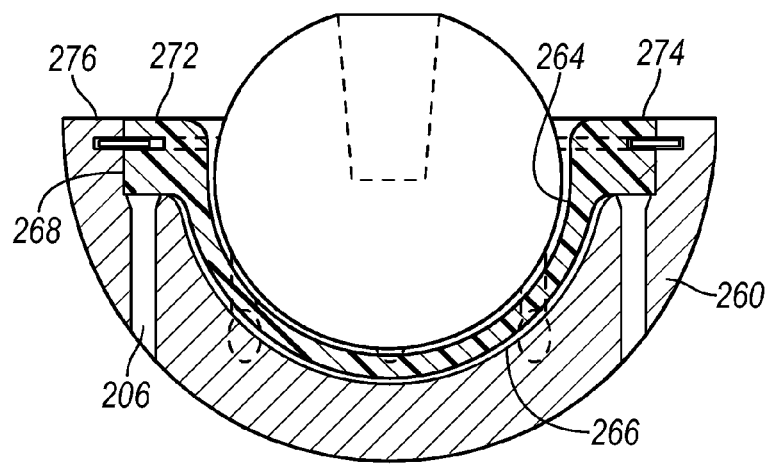

FIGS. 35A and 35B represent an acetabular cup 260 having an associated liner 262. The liner 262, which is configured to be nested within the acetabular cup 260, has a bearing surface 264 which has a radius smaller than the radius of the metal bearing surface 266 of the acetabular cup 260. As best seen in FIG. 35B, the liner 262 has a locking mechanism 268 which defines a retaining slot 270 within a mounting flange 272. The mounting flange 272 is configured to have an upper surface 274 which is generally coplanar with an upper surface 276 of the acetabular cup 260.

Figure 36A:
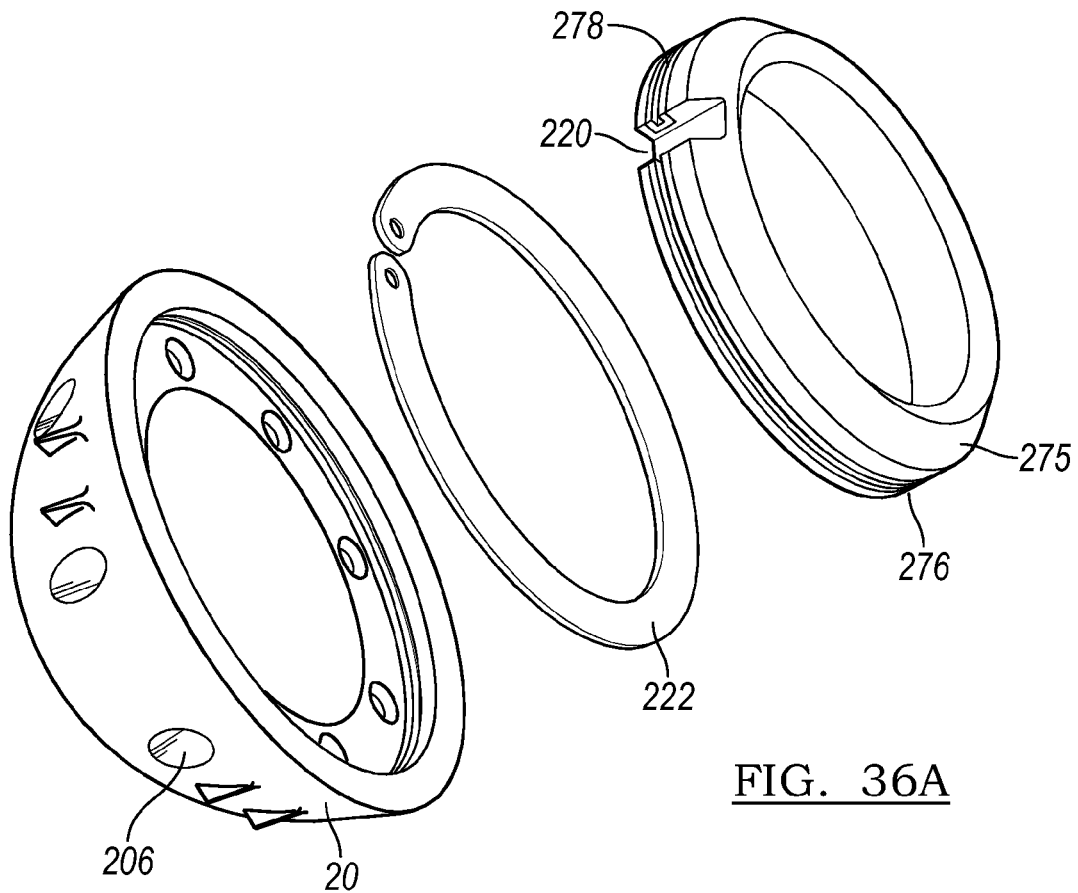
FIGS. 36A and 36B represent a constraining ring having a integrally molded reinforcement structure.
Figure 36B:
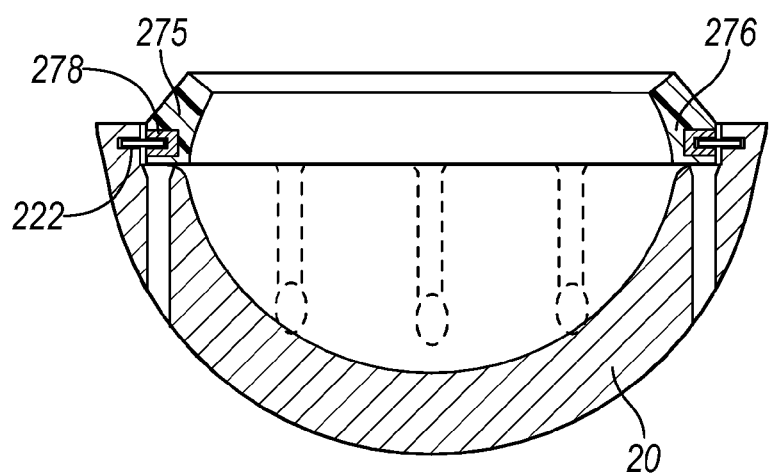

FIGS. 36A and 36B represent a constraining ring 275 having an integral molded reinforcement structure 276. The reinforcement structure 276 is a defined ring having a generally C-shaped cross-section. It is envisioned that the reinforcement structure 276 will be formed of a material having a greater stiffness than the polymer material used to form the constraining ring 275. The C-shaped cross-section, while providing augmented ring stiffness, provides a predefined slot 278 which can be used as a coupling mechanism to couple the constraining ring 275 to the acetabular cup using a snapring 222.

Figure 37A:
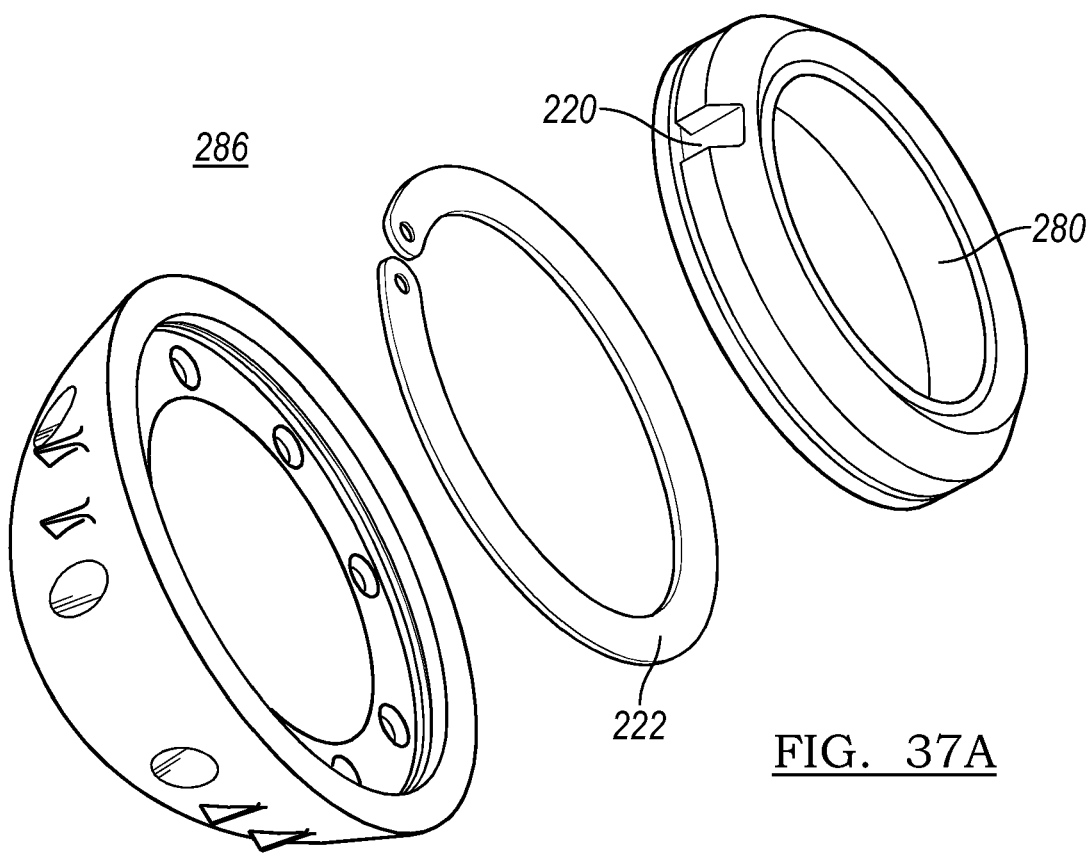
FIGS. 37A and 37B represent a constraining ring having an augmented bearing surface.
Figure 37B:
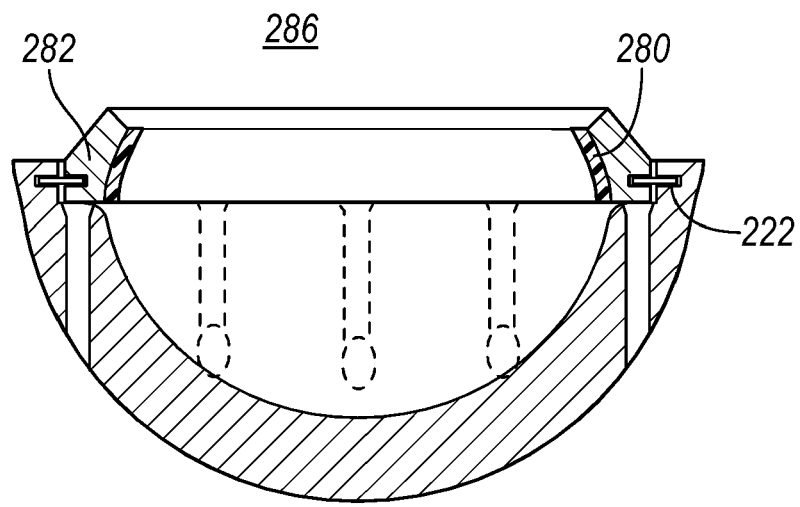

As best seen in FIGS. 37A and 37B, the reinforcement structure can take the form of an augmented bearing surface 280. It is envisioned that the augmented bearing surface 280 can be formed of a material having improved frictional properties, thus allowing the constraining ring 282 to be formed of a material which has stiffness properties better suited for retaining the femoral prosthetic within the acetabular prosthetic 286. The augmented bearing surface can be made of fluoropolymer material such as PTFE, or ceramic or biocompatible metal.

Referring to FIGS. 38A through 38C, an acetabular prosthetic 300 according to the teaching of another embodiment of the present invention is shown. The acetabular prosthetic 300 is generally configured and functions as does the prosthetic shown in FIG. 1. Coupled to the acetabular prosthetic 300 is an alternate constraining ring 302 which interfaces with a modified femoral head 322. As best seen in FIG. 38A, the alternate femoral head 322 has a defined radial surface 324 which can be generally characterized as having a radius which is smaller than the radius of the bearing surface 326 of the femoral head. As further described below, the surface 324 is used to insert the femoral head 322 into the acetabular cup 20 through the constraining ring 302.

The constraining ring 302 has a outer surface 328 which defines a stiffening ring accepting groove 330 and a snap ring accepting groove 332. Disposed within the stiffening ring groove 330 is a metallic stiffening ring 336 which is configured to resist elastic or plastic deformation of the constraining ring. The inner surface 340 of the constraining ring 302 defines a slanted insertion surface 342 and a concave articulating bearing surface 344. Disposed between the bearing surface 344 and the insertion surface 342 is a retaining surface 350. The retaining surface 350 defines an aperture 351 which has a radius which is equal to the radius of the insertion surface 324 of the femoral head 322. Optionally, the retaining surface 350 and the stiffening ring 336 are located at approximately the same predetermined distance away from an interface surface 352 of the constraining ring 302.

Figure 39A:
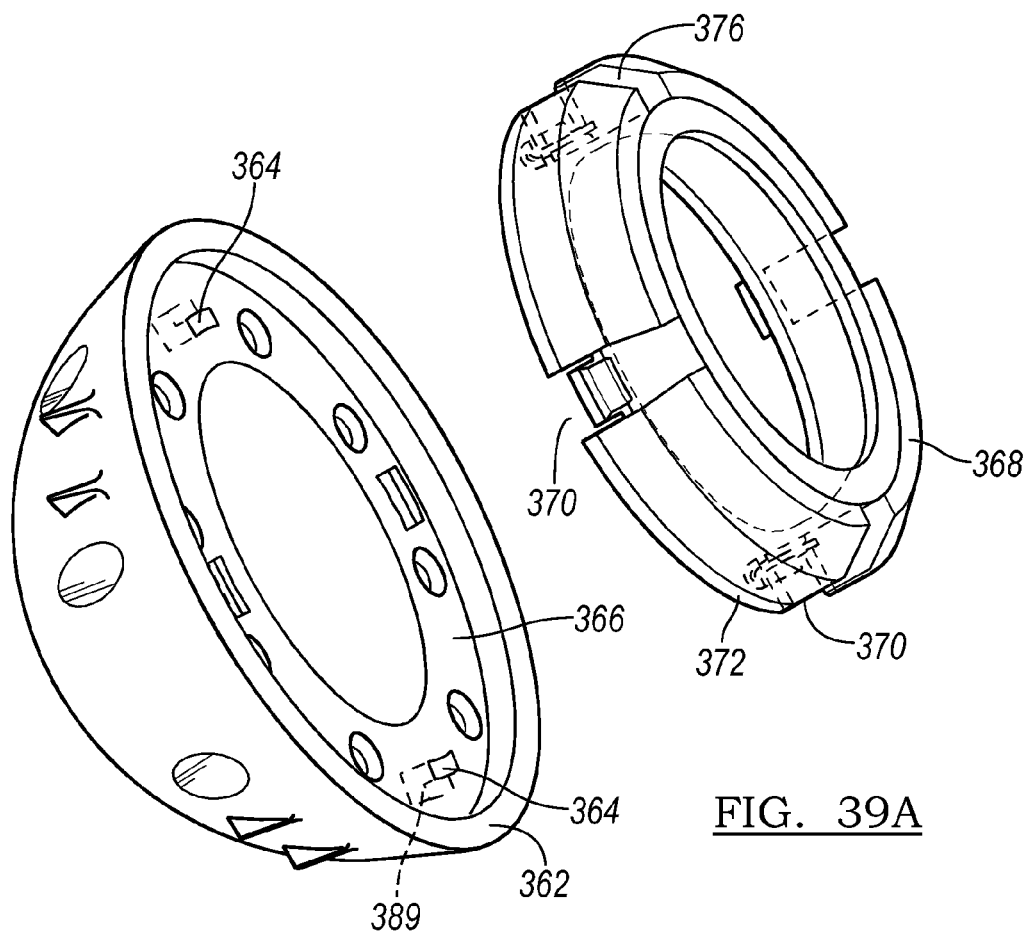
FIGS. 39A, 39B, 40A and 40B represent an alternate acetabular prosthetic having an alternate locking mechanism.
Figure 39B:
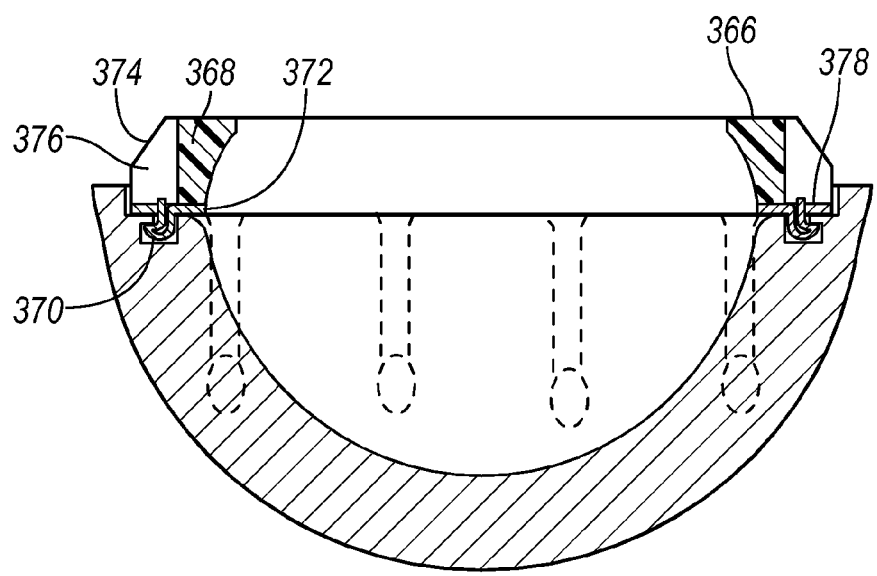
Figure 40A:
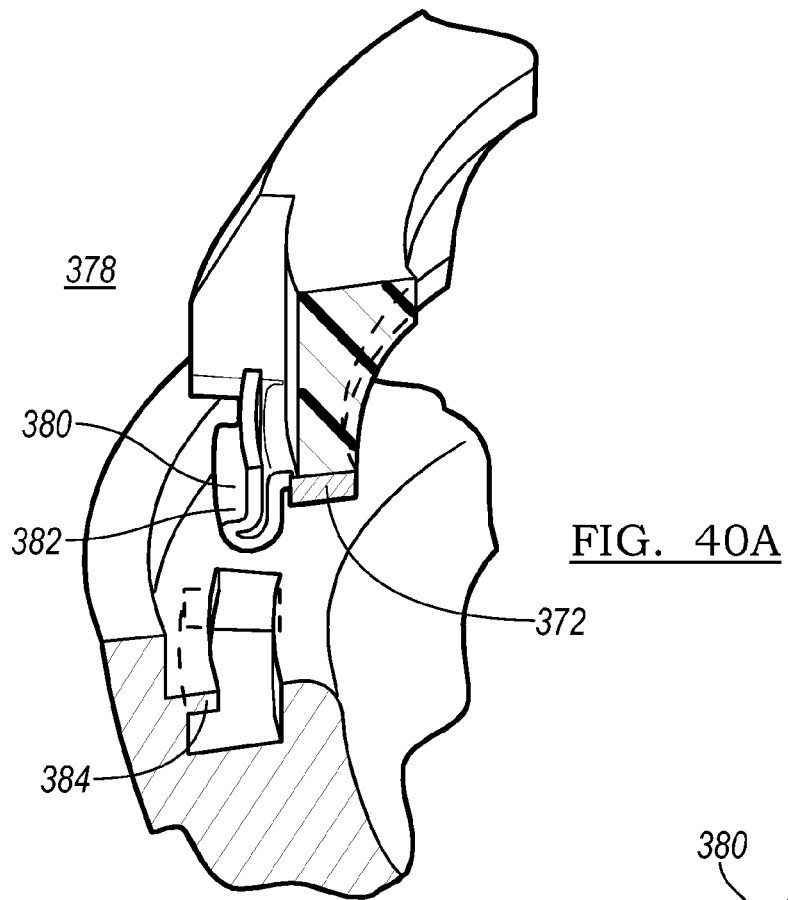
Figure 40B:
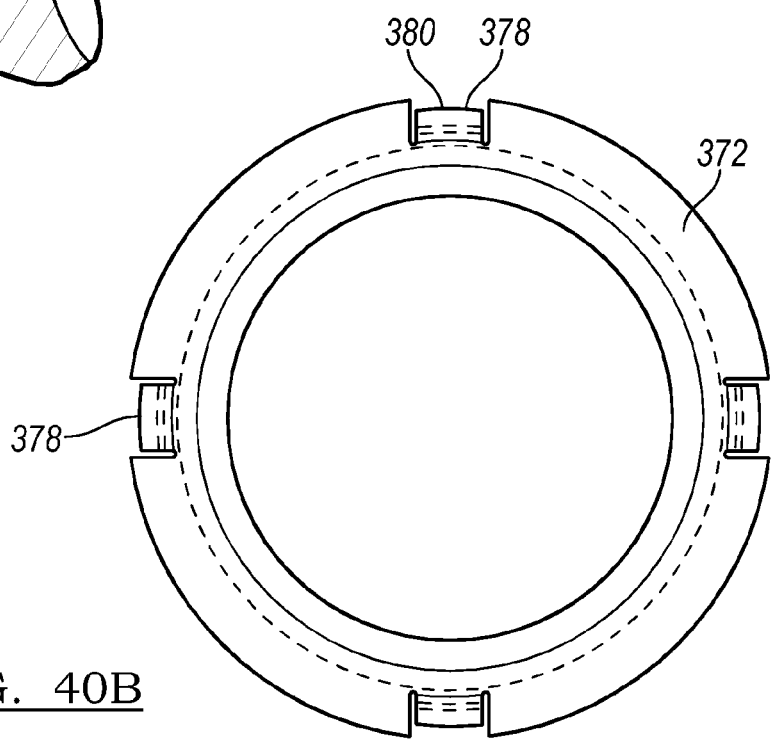

FIGS. 39A through 39C depict an alternate embodiment of the invention. Shown is an acetabular cup 362 having a coupling or locking mechanism 364 defined in the coupling surface 366. The constraining ring 368 is provided having a corresponding locking mechanism 370. The corresponding locking mechanism 370 has a metallic plate 372 integrally molded to the polymer constraining ring 368. An exterior surface 374 of the constraining ring 368 defines at least one aperture 376 which allows access to one or more deformable portions 378 of a deformable tang 380. As best seen in FIGS. 40A and 40B, the deformable tang 380 has an engagement flange 382 which is conformed to lock into a engagement flange or tab 384 formed by the locking mechanism 364 of the acetabular cup 362. It should be noted that while four deformable tang members 380 and locking mechanisms 364 are shown, it is envisioned that any number can be used.

Further envisioned is a kit of prosthetic components which has an acetabular prosthetic defining an integral spherical bearing surface and a locking mechanism configured to accept a second prosthetic device. The kit further has at least one second prosthetic device, namely a constraining ring, a bearing insert, a bearing having an integral constraining ring, each one having a spherical bearing surface which is configured to substantially surrounds a head of a femoral component.

The description of the invention is merely exemplary in nature and, thus, variations that do not depart from the gist of the invention are intended to be within the scope of the invention. For example, while various constraining rings are shown being used with the metal to metal bearing system, it is equally envisioned that these constraining rings can be used with acetabular cups having ceramic, metal, or polymer bearing inserts. Such variations are not to be regarded as a departure from the spirit and scope of the invention.

What is claimed is:

1. An acetabular prosthetic comprising:
   a first prosthetic having a bone engagement surface, a first inner integral generally spherical polished concave bearing surface configured to directly engage an articulating surface of a femoral component, a locking mechanism; and
   a second prosthetic having a second spherical concave bearing surface, said second prosthetic being configured to be disposed between the generally spherical polished concave bearing surface and an articulating surface of a femoral component, wherein said locking mechanism is configured to fixably couple the second prosthetic to the generally spherical polished concave bearing surface so as to prevent relative movement therebetween, wherein the acetabular prosthetic is configured such that the generally spherical polished concave bearing surface engages the articulating surface of the femoral component in a first configuration or the second spherical concave bearing surface engages the articulating surface of the femoral component in a second configuration, in the second configuration said second prosthetic is selectively engaged with said first prosthetic to allow direct engagement of the articulating surface of the femoral component with the second spherical concave bearing surface.

2. The acetabular prosthetic according to claim 1 wherein said second prosthetic is selected from a group of a constraining ring with a bearing insert, a bearing insert, and a bearing insert having an integral constraining ring.

3. The acetabular prosthetic according to claim 1 further comprising a peripheral surface, which defines said locking mechanism, and wherein said peripheral surface defines at least one aperture configured to accept a coupling fastener.

4. The acetabular prosthetic according to claim 1 wherein said second prosthetic implant comprises a polymer bearing surface.

5. The acetabular prosthetic according the claim 4 wherein said second prosthetic is a bearing insert.

6. The acetabular prosthetic according to claim 5 wherein said bearing insert comprises an integral constraining ring.

7. The acetabular prosthetic according to claim 6 wherein said bearing insert defines a bearing insert coupling groove configured to accept a locking ring.

8. The acetabular prosthetic according to claim 1 wherein said second prosthetic comprises a constraining ring.

9. The acetabular prosthetic according to claim 8 wherein said constraining ring includes a hemi-spherical bearing surface.

10. The acetabular prosthetic according to claim 8 wherein said constraining ring defines a constraining ring groove configured to accept a locking ring to couple said constraining ring to said first prosthetic.

11. The acetabular prosthetic according to claim 8 wherein said constraining ring defines a locking flange, said locking flange being configured to mate with said locking mechanism.

12. The acetabular prosthetic according to claim 8 wherein said constraining ring comprises a metal reinforcement ring.

13. An acetabular prosthetic according to claim 8 wherein said constraining ring comprises a restraining lip.

14. The acetabular prosthetic according to claim 8 wherein the constraining ring comprises a plurality of restraining lips.

15. The acetabular prosthetic according to claim 8 wherein the constraining ring comprises an exterior surface which defines a reinforcement accepting groove, said reinforcement accepting groove being configured to retain a reinforcement ring.

16. The acetabular prosthetic according to claim 8 wherein the constraining ring comprises an integrally molded reinforcement structure.

17. The acetabular prosthetic according to claim 16 wherein the reinforcement structure has a C-shaped cross-section.

18. The acetabular prosthetic according to claim 16 wherein the reinforcement structure is a bearing insert.

19. The acetabular prosthetic according to claim 8 wherein the constraining ring comprises a coupling plate having a plurality of elastically deformable coupling flanges which are configured to couple to the locking mechanism.

20. The acetabular prosthetic according to claim 1 further comprising a peripheral surface between the bone engaging surface and the concave bearing surface, and wherein said locking mechanism is a locking flange disposed above a portion of peripheral surface and defining a locking groove between the locking flange and the peripheral surface, said locking flange further defining a plurality of alignment notches.

21. The acetabular prosthetic according to claim 1 wherein substantially all of the inner integral surface is a polished concave bearing surface.

22. A kit of prosthetic components comprising:
a femoral prosthetic having an articulating surface;
an acetabular prosthetic defining an integral polished spherical bearing surface configured to directly interface with the articulating surface, and a locking mechanism; and
a second prosthetic having a second spherical concave bearing surface, said second prosthetic being configured to be disposed between the integral polished spherical bearing surface and the femoral prosthetic, wherein said locking mechanism is configured to accept the second prosthetic device and prevent relative movement of the second prosthetic device with respect to the integral polished spherical bearing surface, wherein in a first configuration the femoral prosthetic engages the integrated polished spherical bearing surface, and in a second configuration said second prosthetic is engaged with said acetabular prosthetic to allow engagement of the femoral prosthetic articulating surface with the second spherical concave bearing surface.

23. The kit according to claim 22 wherein said second prosthetic device is selected from a group consisting of a constraining ring with a bearing insert, a bearing insert, a bearing having an integral constraining ring.

24. The kit according to claim 22 further comprising a plurality of femoral prosthetic components.

25. The kit according to claim 22 wherein said second prosthetic device comprises a constraining ring defining a constraining ring bearing surface and a constraining ring locking mechanism configured to fixably couple said constraining ring to said acetabular prosthetic.

26. The kit according to claim 22 wherein the second prosthetic device comprises a polymer bearing insert and a bearing insert locking mechanism, wherein said bearing insert locking mechanism is configured to lock said polymer bearing insert to said acetabular prosthetic.

27. The acetabular prosthetic according to claim 22 wherein the acetabular prosthetic defines a peripheral surface adjacent to the first bearing surface, said locking mechanism is a locking flange defining a plurality of alignment notches, and defining a locking groove between the locking flange and the peripheral surface.

28. A method for implanting a medical device comprising:
implanting a first prosthetic to a prepared joint, said first prosthetic having a locking mechanism and an integral polished internal bearing surface configured to directly interface with a femoral bearing;
implanting a second prosthetic having a second spherical concave bearing surface between the integral polished internal bearing surface and the femoral bearing, wherein said locking mechanism fixably accepts the second prosthetic and prevents relative movement of the second prosthetic with respect to the integral polished internal bearing surface; and
inserting the metallic femoral bearing within a cavity defined by the integral internal bearing surface of the first prosthetic.

29. The method according to claim 28 further comprising coupling the second prosthetic to the locking mechanism after the first prosthetic device has been implanted in the prepared joint.

30. The method according to claim 29 further comprising coupling said second prosthetic having an integral constraining ring to the locking mechanism.

31. The method according to claim 28 further comprising coupling said second prosthetic to said locking mechanism.

32. The method according to claim 28 further comprising coupling a constraining ring to said locking mechanism.

33. The method according to claim 28 further comprising:
removing the femoral prosthesis from said first prosthetic;
coupling said second prosthetic to said first prosthetic; and
inserting the femoral prosthesis into said first and second prosthetics.

34. An acetabular prosthetic implant comprising:
a first member having a bone engagement surface and an integral generally spherical polished first bearing surface configured to interface with an articulating surface of a femoral prosthetic, said first member defining a locking mechanism; and
a second member, adapted to be coupled to said locking mechanism so as to prevent relative movement of the second member with respect to the first member, said second member defining a second semi-spherical bearing surface, said first and second bearing surfaces defining a generally capsule shaped cavity elongated along a predetermined axis; and wherein said generally capsule shaped cavity is configured to rotatably accept a head of a femoral prosthetic and allow the translation of the head along the predetermined axis, wherein in a first configuration the femoral prosthetic engages the first member, and in a second configuration said second member is engaged with said first member to allow engagement of the articulating surface of the femoral prosthetic with the second semi-spherical concave bearing surface.

* * * * *